(12) United States Patent
Bodner

(10) Patent No.: US 12,310,563 B2
(45) Date of Patent: May 27, 2025

(54) RETROGRADE ENDOSCOPE AND METHOD FOR PERFORMING INTRANASAL ENDOSCOPY

(71) Applicant: Daryl Bodner, Millersville, PA (US)

(72) Inventor: Daryl Bodner, Millersville, PA (US)

(*) Notice: Subject to any disclaimer, the term of this patent is extended or adjusted under 35 U.S.C. 154(b) by 941 days.

(21) Appl. No.: 17/279,570

(22) PCT Filed: Oct. 4, 2019

(86) PCT No.: PCT/US2019/054658
§ 371 (c)(1),
(2) Date: Mar. 24, 2021

(87) PCT Pub. No.: WO2020/072879
PCT Pub. Date: Apr. 9, 2020

(65) Prior Publication Data
US 2021/0338063 A1    Nov. 4, 2021

Related U.S. Application Data

(60) Provisional application No. 62/742,245, filed on Oct. 5, 2018.

(51) Int. Cl.
*A61B 1/233* (2006.01)
*A61B 1/00* (2006.01)
(Continued)

(52) U.S. Cl.
CPC .......... *A61B 1/233* (2013.01); *A61B 1/00073* (2013.01); *A61B 1/00082* (2013.01); *A61B 1/005* (2013.01); *A61B 1/01* (2013.01); *A61B 1/018* (2013.01); *A61B 1/24* (2013.01); *A61M 16/0461* (2013.01); *A61M 16/0666* (2013.01)

(58) Field of Classification Search
CPC .......... A61B 1/233; A61B 1/24; A61B 1/267; A61B 1/005; A61B 1/0051; A61B 1/0052; A61B 1/0053; A61B 1/0055; A61B 1/0056; A61B 1/0057; A61B 1/0058; A61B 1/00073; A61B 1/00082; A61B 1/01;
(Continued)

(56) References Cited

U.S. PATENT DOCUMENTS 4,640,273 A * 2/1987 Greene ..................... A61B 1/24
                                                        128/207.14
4,681,094 A * 7/1987 Rolnick ................... A61B 1/06
                                                          600/187
(Continued)

OTHER PUBLICATIONS

International Search Report and Written Opinion issued in PCT/US2019/054658, dated Feb. 4, 2020.
(Continued)

*Primary Examiner* — Ryan N Henderson
(74) *Attorney, Agent, or Firm* — Blank Rome LLP

(57) ABSTRACT

An assembly for performing intranasal endoscopy on a patient includes a mouth gag defining a central cavity, where the mouth gag is configured to be at least partly received in an oral cavity of the patient, and an outer cannula defining a central lumen, where the outer cannula is configured to be introduced through the central cavity of the mouth gag. The assembly also includes an endoscope extending through the central lumen of the outer cannula and configured to be advanced into a nasal cavity of the patient.

21 Claims, 27 Drawing Sheets

(51) Int. Cl.
*A61B 1/005* (2006.01)
*A61B 1/01* (2006.01)
*A61B 1/018* (2006.01)
*A61B 1/24* (2006.01)
*A61M 16/04* (2006.01)
*A61M 16/06* (2006.01)

(58) Field of Classification Search
CPC ... A61B 1/018; A61M 16/04; A61M 16/0461; A61M 16/0666
See application file for complete search history.

(56) References Cited

U.S. PATENT DOCUMENTS

| | | | | |
|---|---|---|---|---|
| 4,778,448 | A * | 10/1988 | Meer | A61J 15/0053 |
| | | | | 604/533 |
| 5,318,017 | A * | 6/1994 | Ellison | A61M 16/0488 |
| | | | | 128/200.24 |
| 6,109,268 | A | 8/2000 | Thapliyal et al. | |
| 6,257,238 | B1 * | 7/2001 | Meah | A61B 1/24 |
| | | | | 128/200.26 |
| 6,321,749 | B1 * | 11/2001 | Toti | A61M 16/04 |
| | | | | 128/207.14 |
| 6,517,549 | B1 * | 2/2003 | Dennis | A61M 16/0493 |
| | | | | 128/200.26 |
| 7,462,175 | B2 * | 12/2008 | Chang | A61B 17/1204 |
| | | | | 604/510 |
| 7,520,876 | B2 * | 4/2009 | Ressemann | A61B 90/50 |
| | | | | 604/510 |
| 8,114,113 | B2 * | 2/2012 | Becker | A61M 25/10 |
| | | | | 604/514 |
| 9,271,631 | B2 * | 3/2016 | Leeflang | A61B 1/00154 |
| 9,662,466 | B2 * | 5/2017 | Gunday | A61B 1/00071 |
| 10,576,231 | B2 * | 3/2020 | Gunday | A61M 16/0443 |
| 10,856,727 | B2 * | 12/2020 | Goldfarb | A61B 1/0051 |
| 11,273,293 | B2 * | 3/2022 | Palushi | A61B 1/06 |
| 2002/0151871 | A1 * | 10/2002 | Gaiser | A61M 16/0493 |
| | | | | 604/528 |
| 2002/0162555 | A1 * | 11/2002 | West | A61B 18/1485 |
| | | | | 128/200.26 |
| 2005/0197529 | A1 | 9/2005 | Hoshihara et al. | |
| 2006/0278238 | A1 | 12/2006 | Borody | |
| 2007/0068535 | A1 * | 3/2007 | Colman | A61B 90/16 |
| | | | | 128/859 |
| 2007/0073269 | A1 * | 3/2007 | Becker | A61M 1/85 |
| | | | | 604/509 |
| 2007/0255101 | A1 * | 11/2007 | Bar-Or | A61B 1/2736 |
| | | | | 600/124 |
| 2008/0027423 | A1 | 1/2008 | Choi et al. | |
| 2008/0230054 | A1 * | 9/2008 | Prineas | A61M 16/0493 |
| | | | | 128/200.26 |
| 2008/0230055 | A1 * | 9/2008 | NaPier | A61M 16/0497 |
| | | | | 128/200.26 |
| 2008/0295849 | A1 * | 12/2008 | Reynolds | A61M 16/0493 |
| | | | | 128/200.26 |
| 2009/0187098 | A1 * | 7/2009 | Makower | A61B 90/36 |
| | | | | 600/101 |
| 2010/0095968 | A1 * | 4/2010 | Ogilvie | A61B 1/00154 |
| | | | | 128/207.14 |
| 2010/0132700 | A1 * | 6/2010 | Filipi | A61B 1/00154 |
| | | | | 128/200.26 |
| 2010/0262033 | A1 * | 10/2010 | Colman | A61B 1/00154 |
| | | | | 600/532 |
| 2011/0288477 | A1 * | 11/2011 | Ressemann | G06F 16/24568 |
| | | | | 604/95.04 |
| 2012/0088971 | A1 * | 4/2012 | Napier | A61M 16/0493 |
| | | | | 600/109 |
| 2012/0283513 | A1 * | 11/2012 | Leeflang | A61M 16/208 |
| | | | | 600/114 |
| 2013/0184532 | A1 | 7/2013 | Goldfarb et al. | |
| 2014/0018615 | A1 * | 1/2014 | Lee | A61B 1/00165 |
| | | | | 600/103 |
| 2014/0275778 | A1 * | 9/2014 | Gunday | A61B 1/00135 |
| | | | | 600/109 |
| 2015/0141997 | A1 * | 5/2015 | Al-Khatib | A61B 17/1688 |
| | | | | 606/80 |
| 2015/0209545 | A1 * | 7/2015 | Houston | A61M 11/005 |
| | | | | 128/200.16 |
| 2016/0262603 | A1 * | 9/2016 | Molnar | A61B 1/233 |
| 2016/0287065 | A1 * | 10/2016 | Ha | A61B 1/00154 |
| 2016/0287445 | A1 * | 10/2016 | Wasicek | A61M 29/02 |
| 2016/0310714 | A1 * | 10/2016 | Jenkins | A61M 25/0041 |
| 2017/0259020 | A1 * | 9/2017 | Gunday | A61B 1/00016 |
| 2018/0008126 | A1 * | 1/2018 | Arai | A61B 1/00133 |
| 2018/0125336 | A1 * | 5/2018 | Goldfarb | A61B 1/07 |
| 2019/0069759 | A1 * | 3/2019 | Govari | A61B 25/09 |
| 2019/0076211 | A1 * | 3/2019 | Palushi | A61M 29/02 |
| 2019/0125375 | A1 * | 5/2019 | Palushi | A61B 1/227 |
| 2019/0159666 | A1 * | 5/2019 | Matlock | A61M 25/09 |
| 2019/0167151 | A1 * | 6/2019 | Palushi | A61B 5/6803 |
| 2019/0167228 | A1 * | 6/2019 | Ebrahimi | A61M 25/005 |
| 2019/0167351 | A1 * | 6/2019 | Salazar | A61B 5/062 |
| 2019/0175887 | A1 * | 6/2019 | Shameli | A61M 25/0113 |
| 2019/0192176 | A1 * | 6/2019 | Palushi | A61M 25/0662 |
| 2019/0274701 | A1 * | 9/2019 | Hamlekhan | A61M 25/10184 |
| 2020/0108238 | A1 * | 4/2020 | Matlock | B26D 1/08 |
| 2020/0197670 | A1 * | 6/2020 | Palushi | A61M 25/10 |
| 2020/0237190 | A1 * | 7/2020 | Kojo | A61B 1/0055 |
| 2022/0211982 | A1 * | 7/2022 | Palushi | A61B 17/3421 |
| 2023/0218301 | A1 * | 7/2023 | Baker | A61B 17/12136 |
| | | | | 606/196 |

OTHER PUBLICATIONS

International Preliminary Report on Patentability and Written Opinion issued in PCT/US2019/054658, dated Apr. 15, 2021.

* cited by examiner

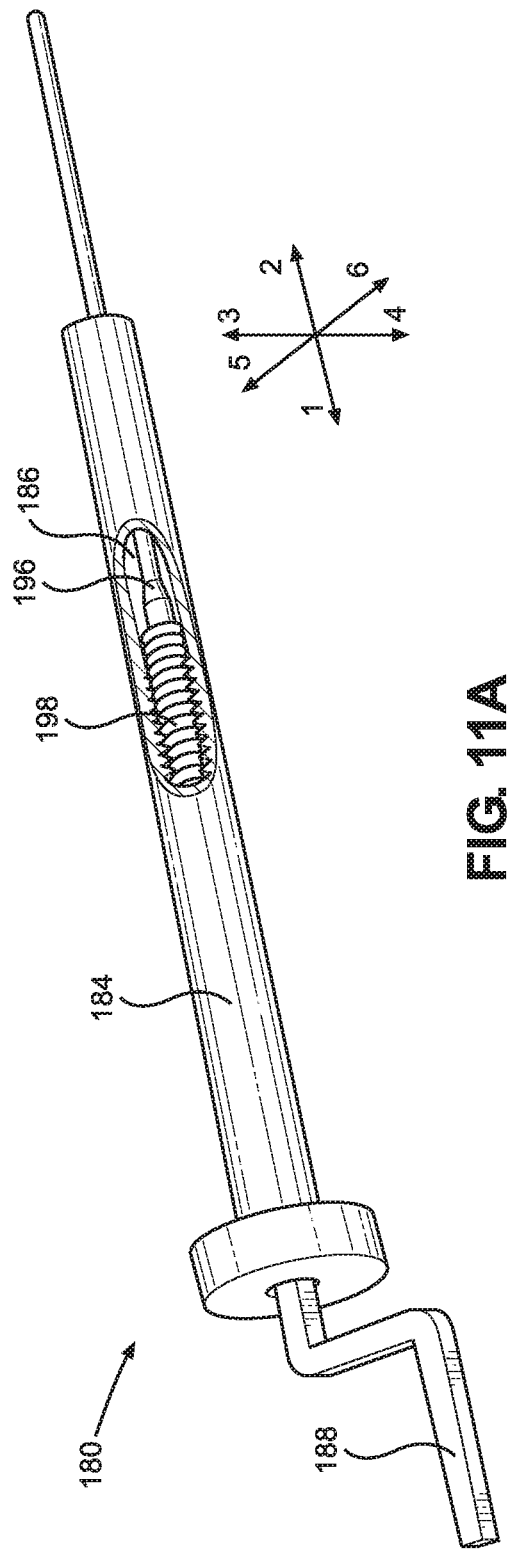
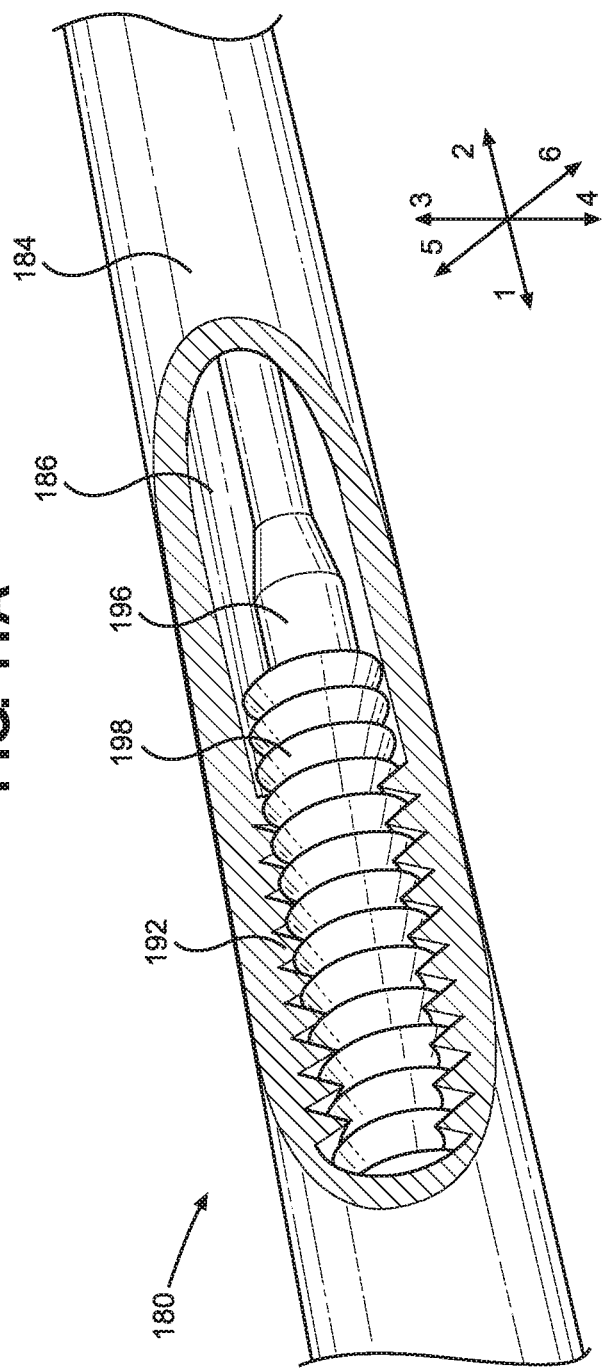
FIG. 11A
FIG. 11B

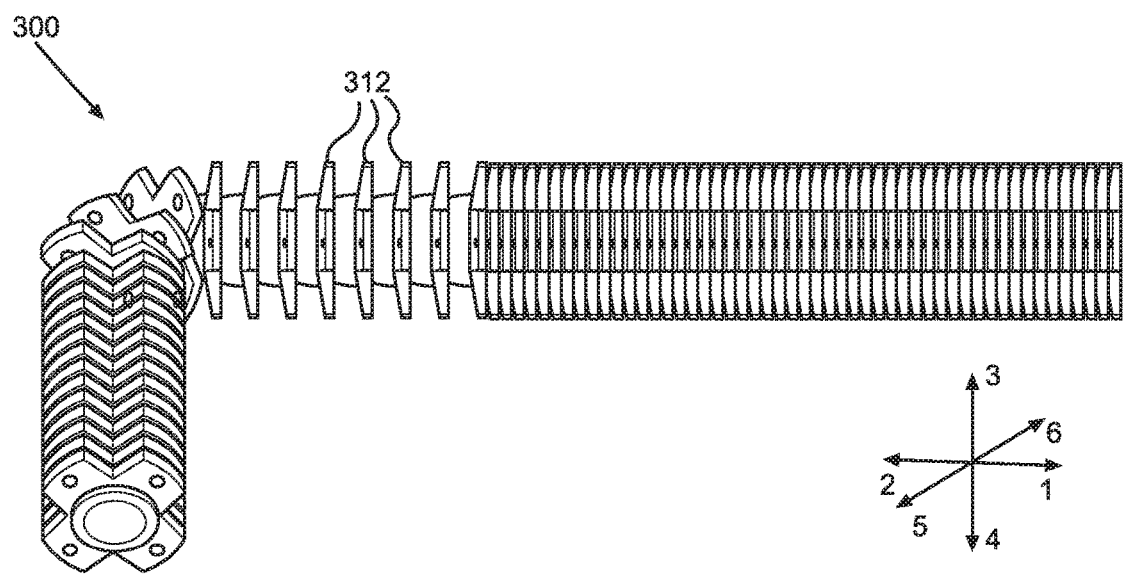
FIG. 19
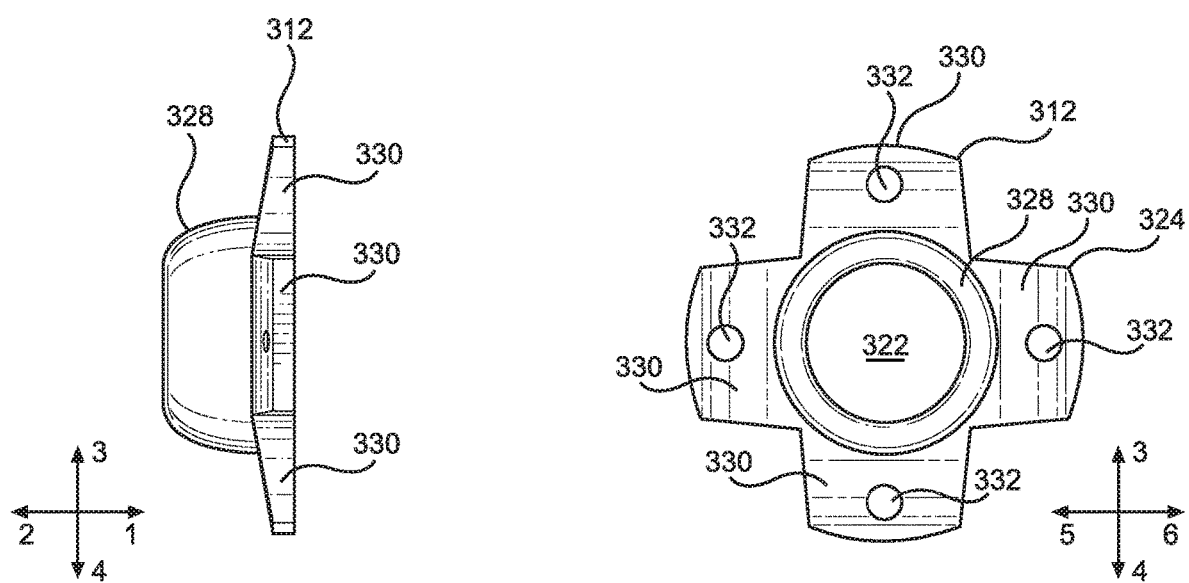
FIG. 20
FIG. 21

RETROGRADE ENDOSCOPE AND METHOD FOR PERFORMING INTRANASAL ENDOSCOPY

CROSS REFERENCE TO RELATED APPLICATIONS

The present application is a U.S. National Stage of International Patent App. No. PCT/US2019/054658, filed Oct. 4, 2019, and published as International Patent Pub. No. WO 2020/072879 A1 on Apr. 9, 2020, which claims the benefit of U.S. Provisional Patent App. No. 62/742,245, filed Oct. 5, 2018, the disclosures of which are hereby incorporated by reference herein.

TECHNICAL FIELD

This application generally relates to assemblies and methods for performing intranasal endoscopy on a patient.

BACKGROUND

Typical endoscopic sinus surgery is performed with endoscopes which are introduced into the anterior nose and which look either directly forward or at a fixed rigid angle. Known endoscopes merely enable visualization in a straight line at an angle to the side, preventing a surgeon from seeing around obstructions. However an anterior approach limits visualization of certain anatomical regions, such as the osteomateal complex, maxillary sinus ostium, possible accessory ostia, maxillary sinus cavity, and the anterior maxillary and inferior anterior walls.

As a result, there is a need for an assembly for performing intranasal endoscopy on a patient that allows for a posterior approach through the oral cavity of a patient.

SUMMARY

An embodiment of the present disclosure is a method for performing intranasal endoscopy on a patient. The method includes advancing an endoscope in a posterior direction through an oral cavity of the patient and advancing the endoscope upwards around a soft palate of the patient. The method also includes advancing the endoscope in an anterior direction that is opposite the posterior direction into a nasal cavity of the patient, and viewing a region of the nasal cavity using the endoscope.

Another embodiment of the present disclosure is an assembly for performing intranasal endoscopy on a patient. The assembly includes a mouth gag defining a central cavity, where the mouth gag is configured to be at least partly received in an oral cavity of the patient, and an outer cannula defining a central lumen, where the outer cannula is configured to be introduced through the central cavity of the mouth gag. The assembly also includes an endoscope extending through the central lumen of the outer cannula and configured to be advanced into a nasal cavity of the patient.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In the drawings:

FIG. 11A is a perspective view of a crank according to an embodiment of the present disclosure;

FIG. 11B is a partial cross-sectional view of the crank shown in FIG. 11A;

FIG. 19 is a perspective view of the endoscope shown in FIG. 17;

FIG. 20 is a side view of a linkage of the endoscope shown in FIG. 19;

FIG. 21 is a top view of the linkage shown in FIG. 20;

DETAILED DESCRIPTION

Figure 1:
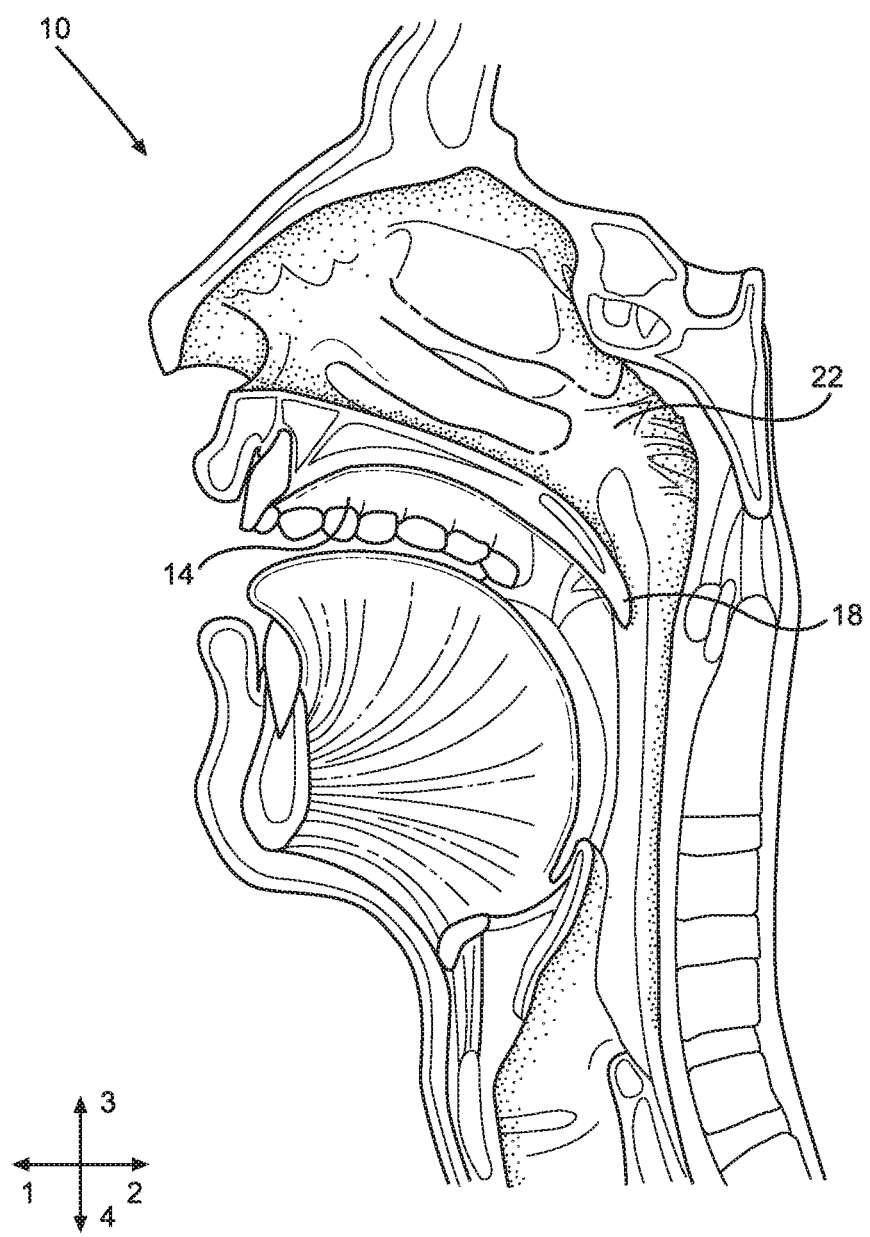
FIG. 1 is a side cross-sectional view of a nasal cavity of a patient.
Figure 2:
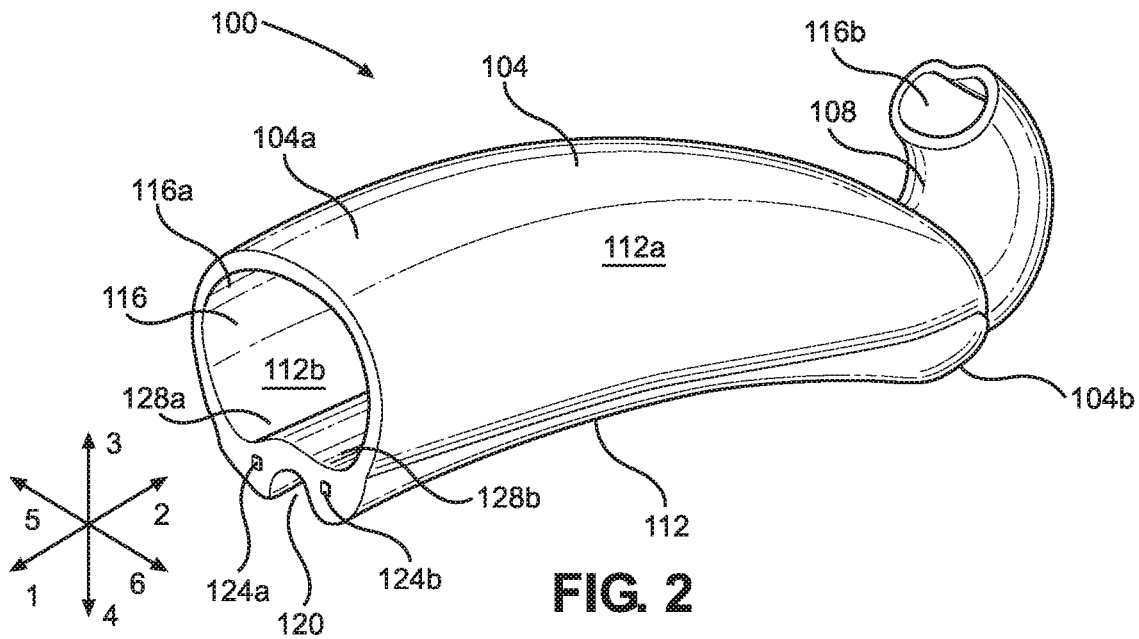
FIG. 2 is a perspective view of a mouth gag according to an embodiment of the present disclosure, with the telescoping extension in an extended position.
Figure 3:
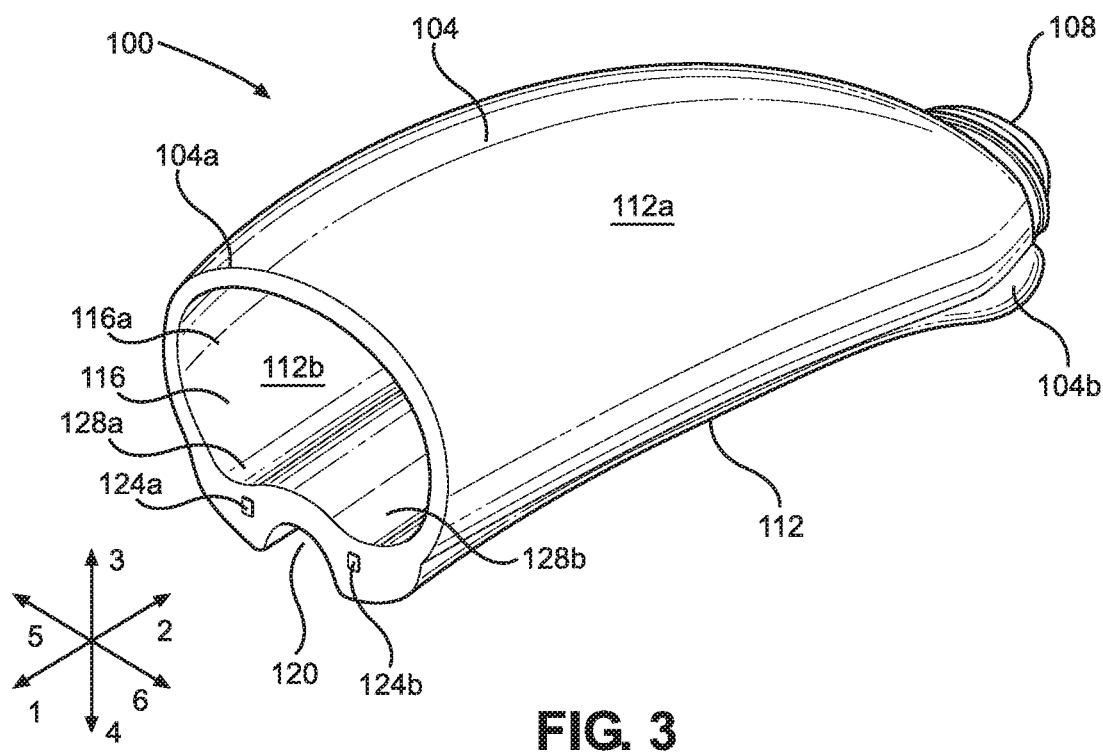
FIG. 3 is a perspective view of the mouth gag shown in FIG. 2, with the telescoping extension in a retracted position.
Figure 4:
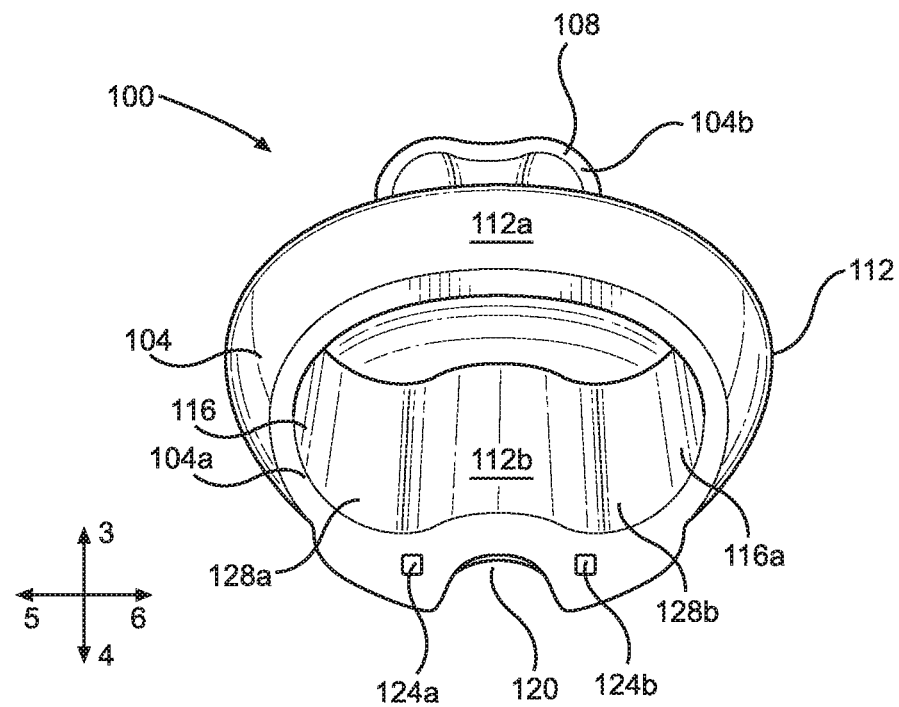
FIG. 4 is a front view of the mouth gag shown in FIG. 2.
Figure 5:
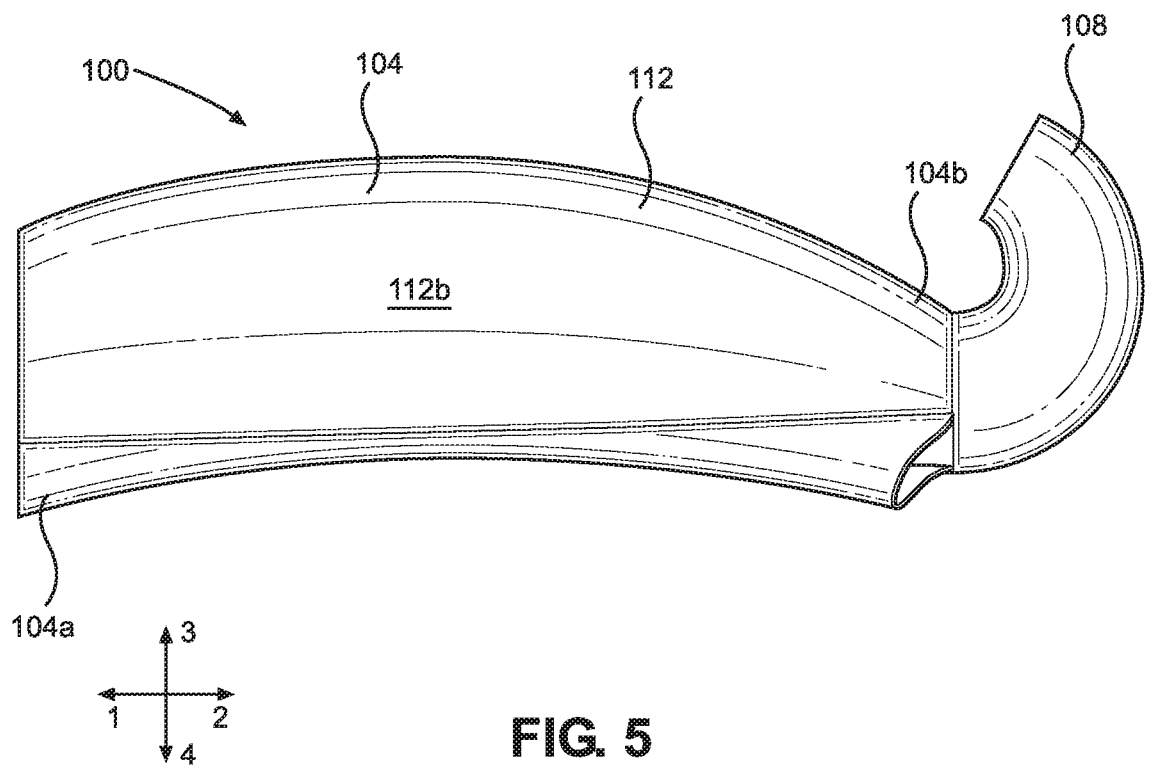
FIG. 5 is a side view of the mouth gag shown in FIG. 2.

Described herein is an assembly 50 for performing intranasal endoscopy comprising a mouth gag 100, an outer cannula 200, and an endoscope 300. Certain terminology is used to describe the assembly 50 in the following description for convenience only and is not limiting. The words "right," "left," "lower," and "upper" designate directions in the drawings to which reference is made. The words "upper" and "lower" refer to directions along the assembly 50 and related parts thereof. The words "inner" and "outer" refer to directions toward and away from, respectively, the geometric center of the description to describe the assembly 50 and related parts thereof. The terminology includes the above-listed words, derivatives thereof, and words of similar import.

Unless otherwise specified herein, the terms "forward," "rearward," "upwards," and "downwards" are used to describe the orthogonal directional components of various components of the assembly 50, as designated by the anterior direction 1, posterior direction 2, superior direction 3, inferior direction 4, right direction 5, and left direction 6. It should be appreciated that while the anterior, posterior, superior, and inferior directions 1-4 are illustrated as extending along a horizontal plane, and the right and left directions 5,6 extend along a vertical plane that is perpendicular to the horizontal plane, the planes that encompass the various directions may differ during use.

The present invention relates to an assembly and methods for performing intranasal endoscopy. FIG. 1 illustrates the head of a patient 10 on whom a nasal procedure is to be performed in cross-section. Typically, both surgical instruments and endoscopes for viewing the region on which a procedure is to be performed, in particular aspects of the sinuses, are inserted into the nasal cavity 22 along the posterior direction 2 through the nose of the patient. Until now, the insertion of an endoscope through the oral cavity 14, around the soft palate 18, and into the nasal cavity 22 for viewing the operating region has not been appreciated.

As noted above, an assembly 50 for performing intranasal endoscopy can include a mouth gag 100, an outer cannula 200, and an endoscope 300. Referring to FIGS. 2-9C, the mouth gag 100 is shown in greater detail. With specific reference to FIGS. 2-5. the mouth gag 100 can include a main body 104 that extends from an anterior end 104a to a posterior end 104b. The main body 104 can be an integrally formed elongate plastic or metallic piece that is sized to be received within an oral cavity 14, as will be discussed further below. The main body 104 defines an outer wall 112 that has an outer side 112a and an inner side 112b opposite the outer side 112a, where the outer side 112a can be contoured to smoothly contact the inner surface of a patient's mouth. The mouth gag 100 can also include a central cavity 116 that extends through the main body 104 from the anterior end 104a to the posterior end 104b, where the inner side 112b of the outer wall 112 faces the central cavity 116. Specifically, the central cavity 116 extends from an input opening 116a at the anterior end 104a of the main body 104 of the mouth gag 100 to an output opening 116b at the posterior end 104b, which is defined by a telescoping extension 108. The central cavity 116 can have a substantially oval cross-section, which may generally correspond to the cross-section of the oral cavity 14. The central cavity 116 is configured to receive a variety of other components of the assembly 50, such as the outer cannula 200 and endoscope 300, which will be discussed below, as they extend through the mouth gag 100 to other regions of the patient 10. The central cavity 116 can define a majority of the cross-section of the main body 104, providing an operator of the assembly 50 ample space to maneuver components of the assembly 50.

The outer side 112a of the main body 104 can define a outer groove 120 that extends into the outer wall 112 and extends posteriorly from the anterior end 104a towards the posterior end 104b. The outer groove 120 can be semi-circular, such that the outer groove 120 configured to receive an endotracheal tube 418 that functions to maintain an open airway during a procedure requiring intranasal endoscopy. Though an endotracheal tube 418 is specifically shown, the outer groove 120 can also be configured to receive a flexible laryngeal mask airway (LMA) tube. While shaped and sized to receive an endotracheal tube 418 (see FIGS. 30A-30D), the outer groove 120 can also be shaped and sized so as to secure the endotracheal tube 418 to the mouth gag 100, which can help prevent extubation throughout the procedure. Though depicted as located along the inferior central side of the outer wall 112, it is contemplated that the outer groove 120 can be defined along other areas of the outer wall 112 as desired. Additionally, the main body 104 can include first and second inner grooves 128a, 128b defined by the inner side 112b of the outer wall 112, where the first inner groove 128a is spaced from the outer groove 120 along the right direction 5, while the second inner groove 128b is spaced from the outer groove 120 along the left direction 6. The first and second inner grooves 128a, 128b can be utilized to direct the outer cannula 200 and endoscope 300 during intranasal endoscopy, as will be discussed further below.

The mouth gag 100 can include a telescoping extension 108 that is attached to and extends from the posterior end 104b of the main body 104 along the posterior and superior directions 2, 3. The telescoping extension 108 can have a substantially curved shape, such that when the main body 104 of the mouth gag 100 is placed within the oral cavity 14, the telescoping extension 108 can extend around the soft palate 18 of the patient and into the nasopharynx. The telescoping extension 108 can function to provide the outer cannula 200 and endoscope 300 with an unencumbered path around the soft palate 18 and into the nasal cavity 22, as well as stabilize the overall assembly 50 and protect the tissue of the soft palate 18 and surrounding features. Additionally, the outer cannula 200 can stabilize the endoscope 300 so that it has adequate rigidity in the operative field. The telescoping extension 108 can extend from a leading end 108a configured to extend into the nasopharynx to a trailing end 108b attached to the main body 104. To allow for the mouth gag 100 to be easily placed within the oral cavity 14 of the patient 10, the telescoping extension 108 can initially be in a retracted position, in which the telescoping extension 108 is partially or completely within the central cavity 116 of the main body 104, and thus substantially within the cross-sectional profile of the main body 104. Once the main body 104 of the mouth gag 100 is substantially within the oral cavity 14, the telescoping extension 108 can be transitioned from a retracted position to an extended position, in which the leading end 108a of the telescoping extension 108 extends around the soft palate 18 and into the nasopharynx, as will be described further below.

Figure 6A:
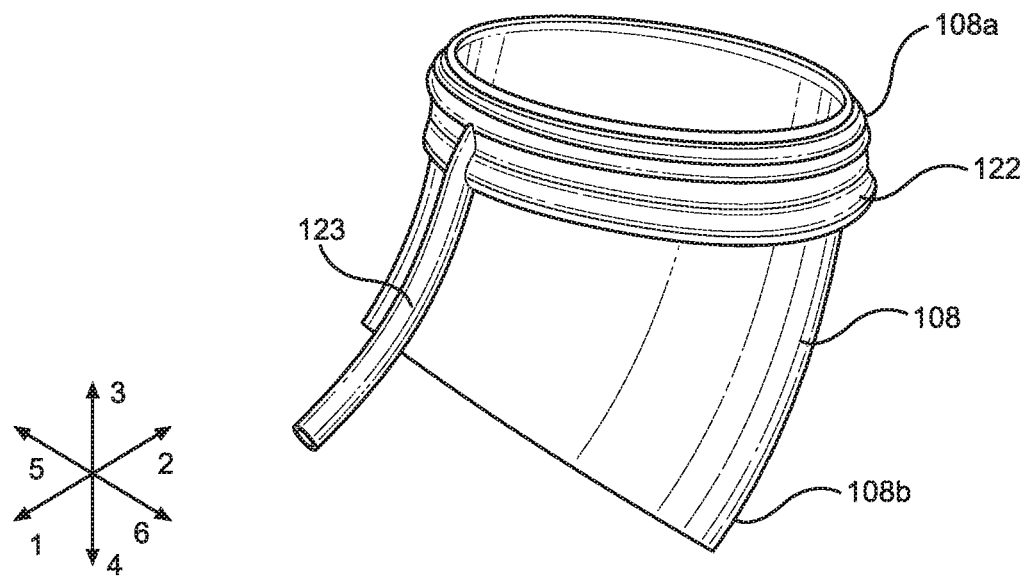
FIG. 6A is a perspective view of a telescoping extension according to an embodiment of the present disclosure, with an inflatable balloon cuff in a deflated configuration.
Figure 6B:
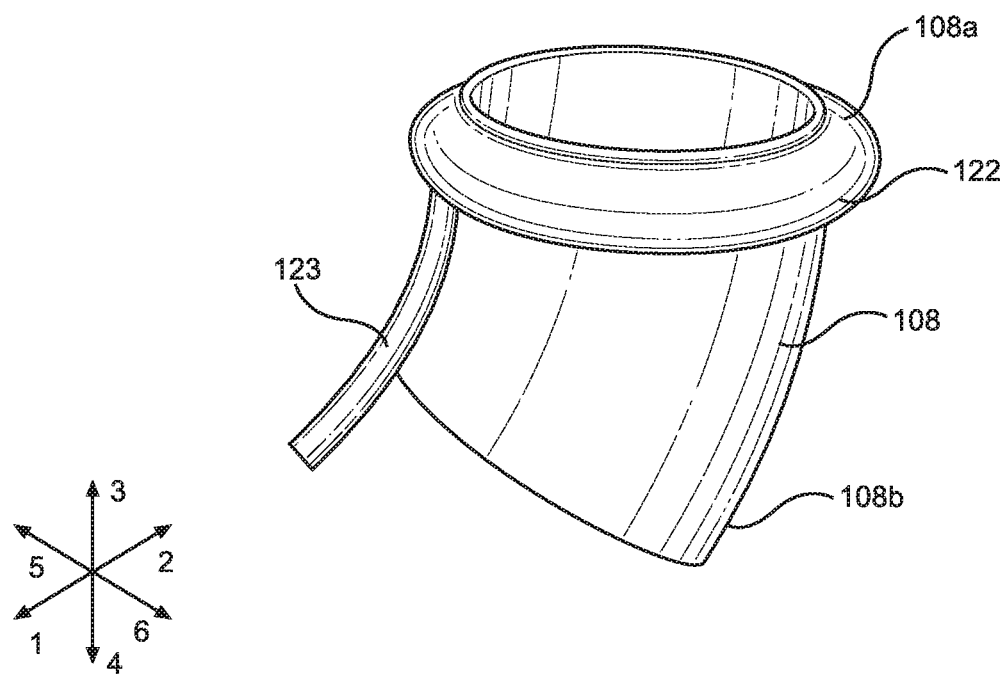
FIG. 6B is a perspective view of the telescoping extension shown in FIG. 6A, with the inflatable balloon cuff in an inflated configuration.

As shown in FIGS. 6A-6B, the telescoping extension 108 can include an inflatable balloon cuff 122 attached to the leading end 108a. The balloon cuff 122 can comprise a plastic or polymer body, and can be freely inflated and deflated by a user of the assembly 50 as desired. A tube 123 can extend from the balloon cuff 122, through the telescoping extension 108 and the main body 104, and to a pressurized air source external to the patient 10, such as a syringe, hand pump, motorized air pump, etc., thus providing the balloon cuff 122 with a pathway for selectively receiving pressurized air. As such, the balloon cuff 122 can transition between an inflated configuration and a deflated configuration. The balloon cuff 122 can be in the deflated configuration throughout the insertion of the mouth gag 100 into the oral cavity 14 and transition of the telescoping extension 108 from the retracted position to the extended position. Further, the balloon cuff 122 can be in the deflated configuration throughout the entirety of an endoscopic procedure. However, the balloon cuff 122 can be transitioned to the inflated configuration so as to occlude the nasopharynx to prevent blood, secretions, irrigation, and tissue debris from leaving the nasal cavity 22 and translating down the back of the patient's throat and into the hypopharynx or larynx. A suction port (not shown) can be incorporated into the balloon cuff 122 to evacuate any such debris. The balloon cuff 122 can also be configured to center and stabilize the position of the leading end 108a of the telescoping extension 108 in the nasopharynx.

Figure 7A:
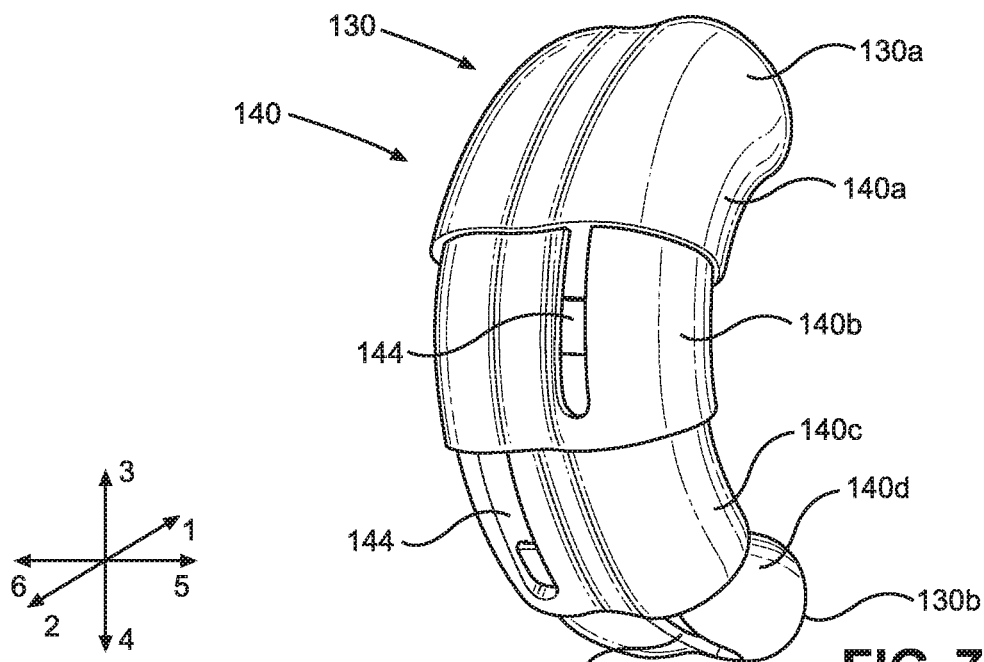
FIG. 7A is a perspective view of a telescoping extension according to an embodiment of the present disclosure, with the telescoping extension in an expanded position.
Figure 7B:
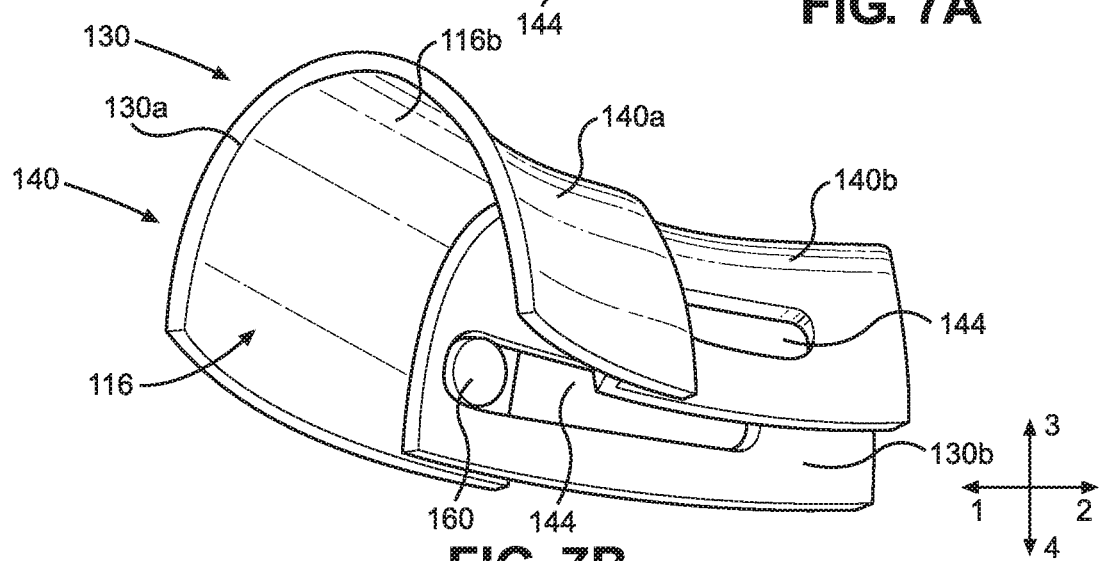
FIG. 7B is an alternative perspective view of the telescoping extension shown in FIG. 7A.
Figure 8A:
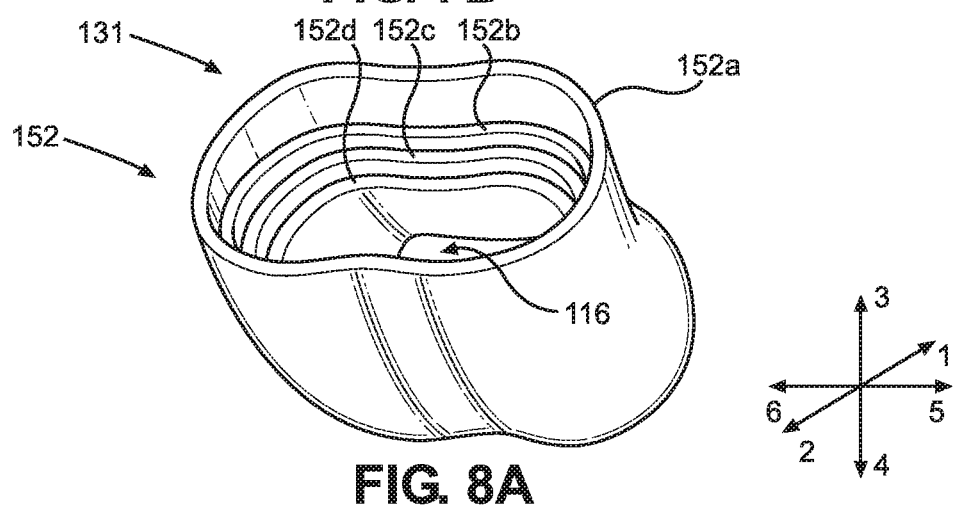
FIG. 8A is a perspective view of a telescoping extension according to another embodiment of the present disclosure.
Figure 8B:
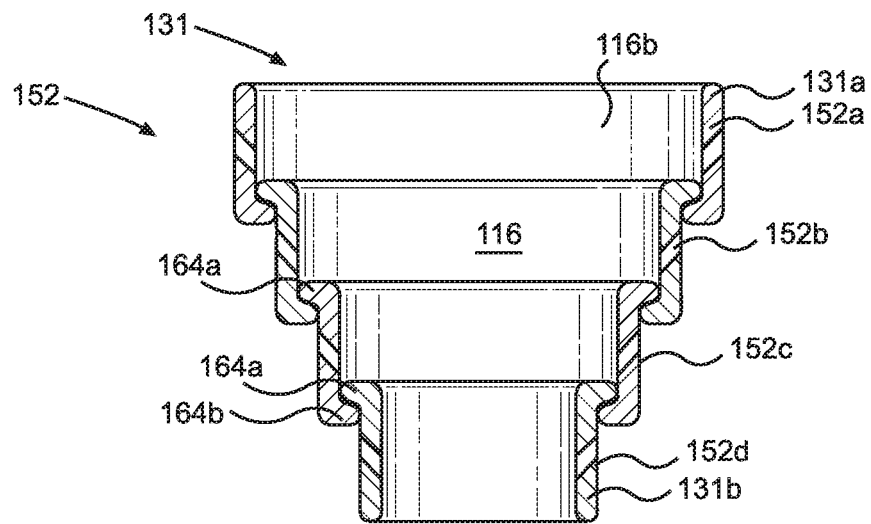
FIG. 8B is a cross-sectional view of the telescoping extension shown in FIG. 8A.
Figure 8C:
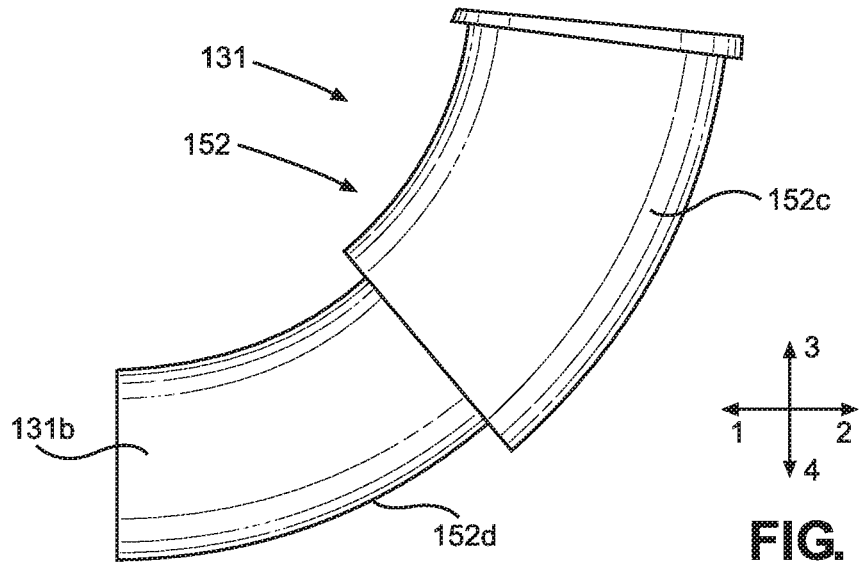
FIG. 8C is a side view of the telescoping extension shown in FIG. 8A.
Figure 8D:
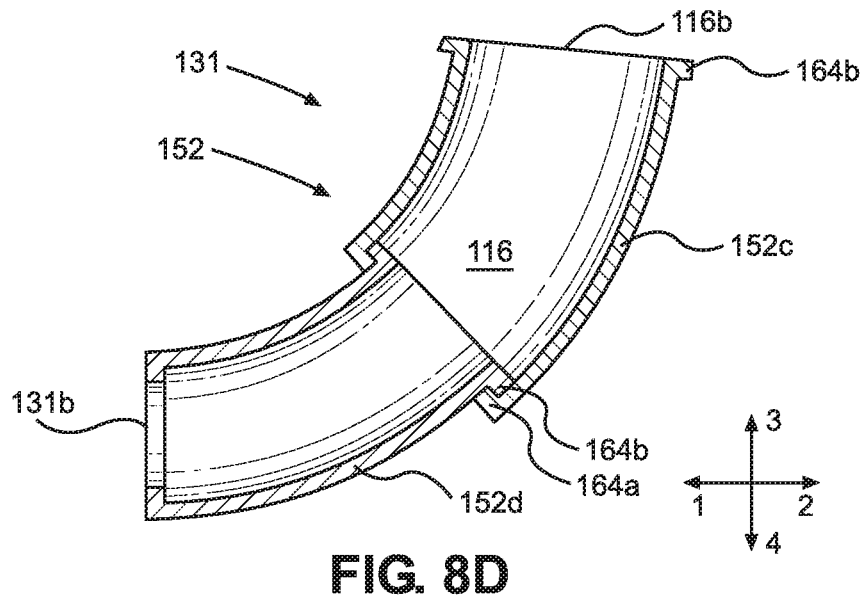
FIG. 8D is a cross-sectional view of the telescoping extension shown in FIG. 8A.

Though FIGS. 2-6B depict a substantially rigid, monolithic telescoping extension 108, other types and configurations of telescoping extensions are contemplated. As shown in FIGS. 7A-7B, the mouth gag 100 can include a telescoping extension 130 that extends from a leading end 130a to a trailing end 130b that is configured to be attached to the main body 104 of the mouth gag 100. The telescoping extension 130 can define a body 140 comprised of four separate segments that are interlocked but movable with respect to each other. As shown, the telescoping extension 130 includes a first segment 140a that includes the leading end 130a, a second segment 140b attached to the first segment 140a, a third segment 140c attached to the second segment 140b, and a fourth segment 140d that includes the trailing end 130b and is attached to the third segment 140c. In an extended position, the telescoping extension 130 can define a substantially semi-annular shape. In a retracted position, the first segment 140a can collapse so that each of the segments 140b-140d is completely within the profile of the first segment 140a. Though the telescoping extension 130 is specifically described as including four segments 140a-140d, the telescoping extension can include more or less than four segments as desired.

As the segments 140a-140d define an oval cross-section, the segments 140a-140d may only translate along the axis of the central cavity 116 in relation to each other, and thus have no degree of relative rotational movement. Further, the movement of the segments 104a-104d in relation to each other can be constrained by slots 144 shaped to receive protrusions 160 extending from an adjacent segment. For example, the second segment 140b can define a slot 144 that receives a protrusion 160 extending from the inner surface of the first segment 140a, the third segment 140c can define a slot 144 that receives a protrusion 160 extending from the inner surface of the second segment 140b, and the fourth segment 140d can define a slot 144 that receives a protrusion 160 extending from the inner surface of the third segment 140c. As the telescoping extension 130 transitions between the extended and retracted position, the protrusions 160 translate within their respective slots so as to guide the movement of the segments 140a-140d relative to each other.

FIGS. 8A-8D depict another embodiment of a telescoping extension 131 that extends from a leading end 131a to a trailing end 131b that is configured to be attached to the main body 104 of the mouth gag 100. The telescoping extension 131 can define a body 152 comprised of four separate segments that are interlocked but moveable with respect to each other. Though the telescoping extension 131 is explicitly shown as including four segments, the telescoping extension 131 can include more or less extensions as desired. As shown, the telescoping extension includes a first segment 152a that includes the leading end 131a, a second segment 152b that is attached to the first segment 152a, a third segment 152c that is attached to the second segment 152b, and a fourth segment 152d that is attached to the third segment 152c and includes the trailing end 131b. In an extended position, the telescoping extension 131 can define a substantially semi-annular shape. In a retracted position, the first segment 152a can collapse such that the second, third, and fourth segments 152b-152d are largely within the profile of the first segment 152a.

Additionally, the segments 152a-152d can define respective ridges 164a, 164b that are configured to limit the degree to which the telescoping extension 130 can extend as it transitions from the retracted position to the extended position. For example, each of the segments 140a-140d can include one or both of leading and trailing ridges 164a, 164b. In one embodiment, the first segment 140a can include an inwardly-extending trailing ridge 164b, the second segment 164b can include an outwardly-extending leading ridge 164a configured to engage the inwardly-extending trailing ridge 164b of the first segment 140a, the third segment 140c can include an outwardly-leading ridge 164a configured to engage the inwardly-extending trailing ridge 164b of the second segment 140b, and the fourth segment 140d can include an outwardly-extending leading ridge 164a configured to engage the inwardly-extending trailing ridge 164b of the third segment 140c. However, other embodiments including more or less ridges or differently shaped and configured ridges are contemplated. As the telescoping extension 130 extends, the engagement between the above-described ridges 164a, 164b functions to limit the degree to which the telescoping extension 130 is permitted to lengthen.

Figure 9A:
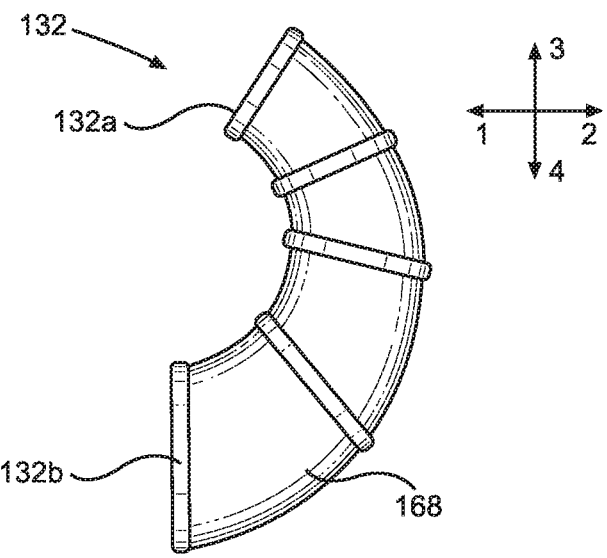
FIG. 9A is a side view of a telescoping extension according to an embodiment of the present disclosure, with the telescoping extension in an extended position.
Figure 9B:
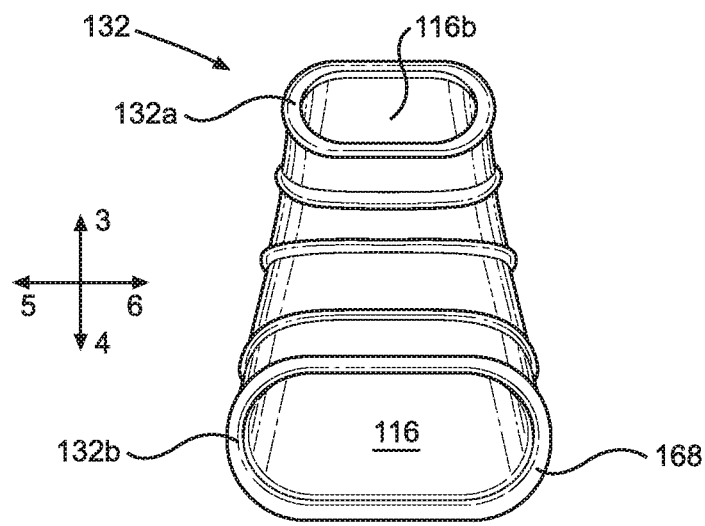
FIG. 9B is a front view of the telescoping extension shown in FIG. 9A.
Figure 9C:
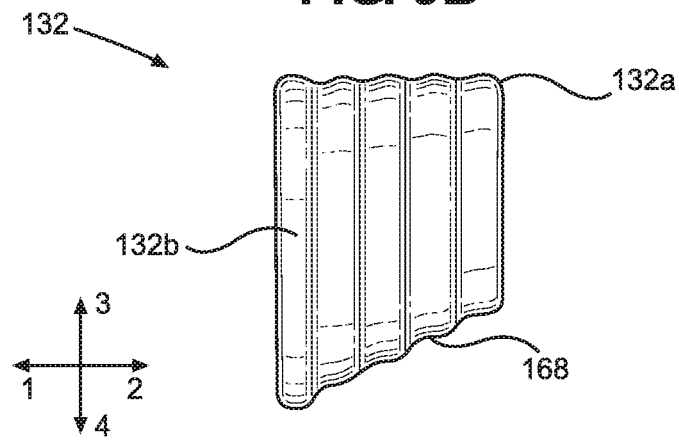
FIG. 9C is a side view of the telescoping extension shown in FIG. 9A, with the telescoping extension in a retracted position.

FIGS. 9A-9B depict another alternative embodiment of a telescoping extension 132 that extends from a leading end 132a to a trailing end 132b that is configured to be attached to the main body 104 of the mouth gag 100. Unlike the telescoping extensions 130, 131, the telescoping extension 132 can define a soft, one-piece expandable and retractable body 168. The body 168 can progressively narrow as it extends from the trailing end 132b to the leading end 132a Alternatively, the body 168 can have an hourglass shape. As shown, the telescoping extension includes a first segment 152a that includes the leading end 131a and a second segment 152b attached to the first segment 152a. In an extended position, the telescoping extension 132 can define a substantially semi-annular shape. Because the body 168 is comprised of a softer material, an operator can move the leading end 132a towards the trailing end 132b so as to collapse the body 168 of the telescoping extension 132, thus resulting in the body 168 having a much smaller profile in the retracted position. As a result, the telescoping extension 132 can largely fit within the central cavity 116 of the main body 104 in the retracted position.

Figure 10A:
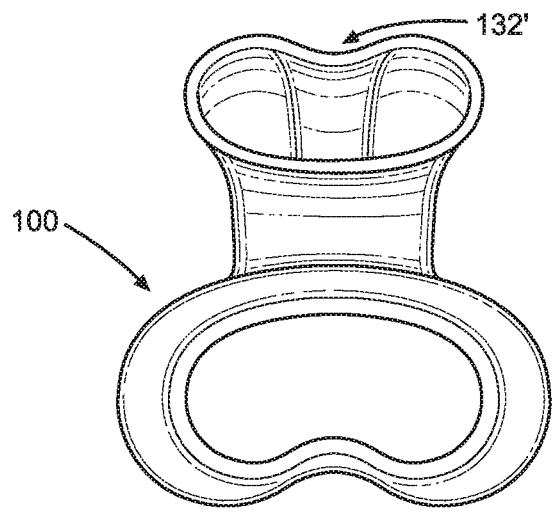
FIG. 10A is a front view of a mouth gag according to an embodiment of the present disclosure.
Figure 10B:
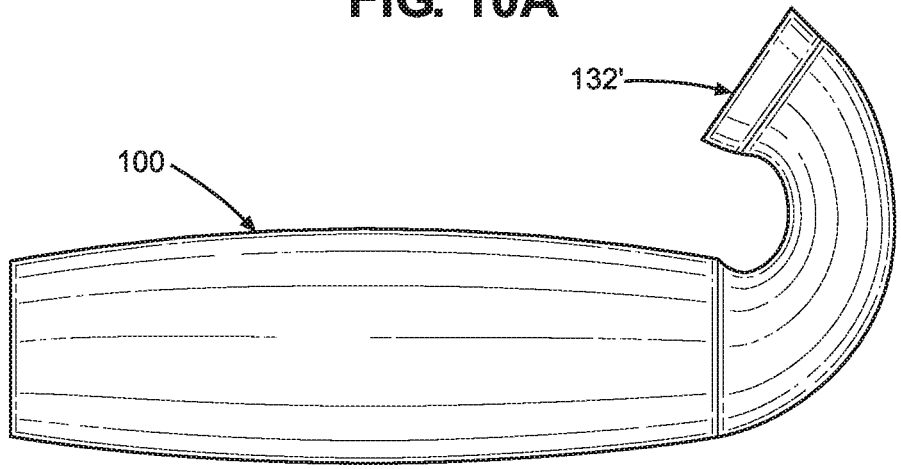
FIG. 10B is a side view of the mouth gag shown in FIG. 10A.
Figure 10C:
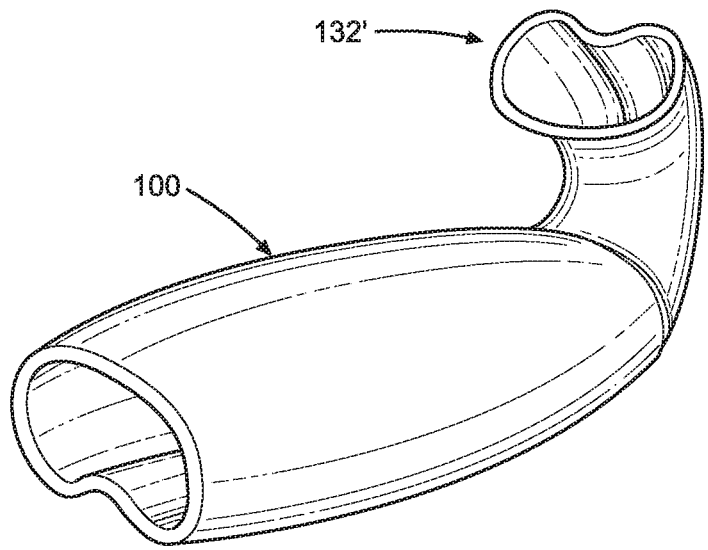
FIG. 10C is a perspective view of the mouth gag shown in FIG. 10A.

FIGS. 10A-10C depict an alternative embodiment of a one-piece telescoping extension 132', where the telescoping extension 132' defines an hourglass-like shape. Like the telescoping extension 132, the telescoping extension 132' can define a soft, one-piece expandable and retractable body. The one-piece designs of the telescoping extensions 132, 132' are compact and pliable, and can prevent the entrapment of soft tissue upon retraction. Further, the hourglass shape of the telescoping extension 132' can aid in placing an endoscope ensemble in the optimal diagonal nasopharyngeal orientation.

Now referring to FIGS. 11A-11B, the assembly 50 can include a crank 180 for transitioning any of the telescopic extensions 108, 130, 131, 132 between the extended and retracted position. The crank 180 can have an elongated tubular body 184 that defines a cavity 186 extending therethrough. The cavity 186 can be sized to contain a shaft 196 that extends through the cavity 186 and is configured to rotate relative to the body 184. The shaft 196 can be the feature that directly engages the telescoping extension 108, where rotation of the shaft 196 relative to the body 184 can transition the telescoping extension between the extended and retracted position. To control rotation of the shaft 196, the inner surface of the body 184 can define a plurality of threads 192 extending radially inwards into the cavity 186 that are configured to engage a plurality of threads 198 extending radially outwards. The engagement between the threads 192 of the body 184 and the threads 198 of the shaft 196 can ensure that rotation of the shaft 196, and thus transitioning of the telescoping extension 108, occurs in a controlled, incremental manner. The shaft 196 can be manually rotated by a user through a handle 188 connected to the shaft 196, though other methods of rotating the shaft 196 are contemplated. The shaft 196 can extend through one of the bores 124a-124b (see FIGS. 2-3) that extend through the main body 104 so as to engage the telescoping extension 108. Though one specific device for transitioning the telescoping extension 108 between the retracted and extended positions is described, it is contemplated that other devices could be utilized. For example, the crank 180 could be replaced with a ratcheting device, hydraulic pistons, expandable ribbons, etc. Further, multiple cranks 180 can be simultaneously utilized. When multiple cranks 180 are utilized, they can either be individually controlled or interconnected so as to be concurrently controlled. The portion of the shaft 196 exterior to the body 184 can transition from a cylindrical cross-section to a flat ribbon-like cross-sectional shape that curves so as to extend into the mouth gag 100, and thus is not capable of axial rotation.

Now referring to FIGS. 12A-16, the outer cannula 200 will be discussed in detail. The outer cannula 200 can have an elongate body 204 that extends from an anterior end 204a to a posterior end 204b opposite the anterior end 204a. During an endoscopic procedure, the anterior end 204a is configured to be located external to the patient 10 while the posterior end 204b can be located within the nasal cavity 22. The body 204 is substantially flexible, such that a user can manually adjust the curvature and orientation of various portions along the body 204, as will be discussed further below.

The outer cannula 200 can comprise a flexible sheath 208 that extends from the anterior end 204a to the posterior end 204b and is configured to be disposed around the internal components of the outer cannula 200. The flexible sheath 208 can be comprised of a sufficiently flexible material so as to conform to the various shapes and configurations of the internal features of the outer cannula 200, while sufficiently protecting and shielding those features from environmental effects. The outer cannula 200 can also comprise a plurality of linkages 212 disposed within the flexible sheath 208 and arranged along the flexible sheath 208. Each of the linkages 212 can be a monolithic, molded plastic or metal component. Each linkage can comprise a body 224 having an outer body 224a and an inner body 224b radially disposed within the outer body 224a. Each of the outer and inner bodies 224a, 224b can have a substantially annular shape, though other shapes are contemplated. The outer and inner bodies 224a, 224b can be connected by a plurality of extensions 228 that extend radially outwards from the inner body 224b and connect to the outer body 224a. Specifically, the body 224 is shown as having four extensions 228, each being equidistantly spaced about the perimeter of the inner body 224b at the "12 o'clock," "3 o'clock," "6 o'clock," and "9 o'clock" positions. However, the body 224 can include more or less extensions as desired. For example, the body 224 can include one, two, three, or more than four extensions. Also, in other embodiments the extensions 228 may not be equidistantly spaced about the perimeter of the inner body 224b.

Each linkage 212 defines a bore extending through the center of the inner body 224b. When aligned within the flexible sheath 208, these bores can collectively define a central lumen 220 that extends through the entirety of the outer cannula 200. The central lumen 220 can define a sufficient volume so as to be configured to receive the endoscope 300, as will be discussed further below. The inner body 224b of each linkage can be tapered inwards as it extends along the posterior direction 2 past the outer body 224a. This allows the posterior end of the inner body 224b of each linkage 212 to nest within the anterior end of the inner body 224b of the next linkage 212 along the length of the outer cannula 200. This nesting arrangement aids in aligning the linkages 212 along the outer cannula 200 and limiting relative translation between the linkages 212, while still allowing relative rotation between adjacent linkages 212 so as to permit curving of the outer cannula 200.

Figure 27:
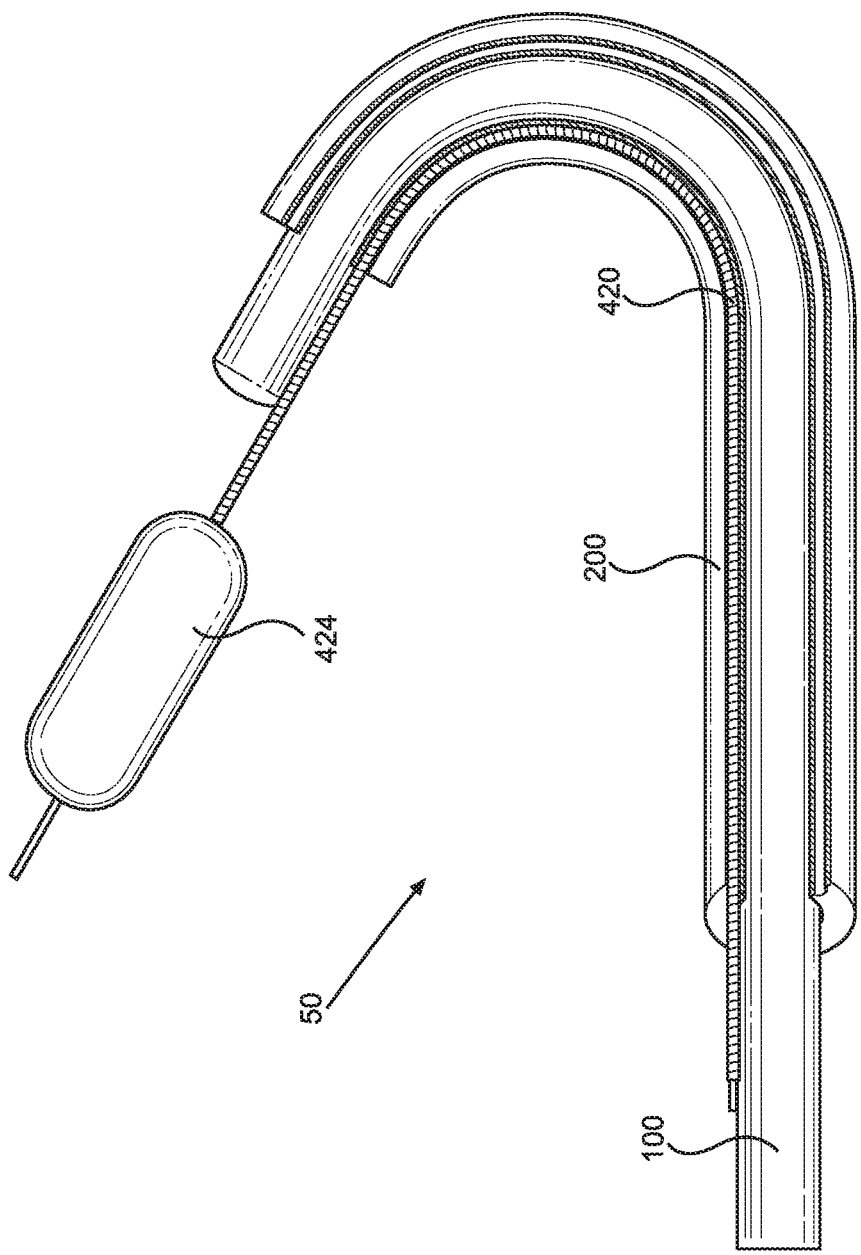
FIG. 27 is a side view of an assembly according to an embodiment of the present disclosure.

Between the outer and inner bodies 224a, 224b of each linkage 212, a plurality of voids 236 can be defined that extend entirely through the linkage 212 from the anterior end to the posterior end. Specifically, each void 236 can be defined between the outer and inner bodies 224a, 224b and two extensions 228 that extend between the outer and inner bodies 224a, 224b. As each linkage 212 is shown as include four extensions 228, and because each extension 228 is equidistantly spaced about the body 224 of the linkage 212, each of the voids 236 can define a radial arc that extends about 90 degrees. However, as the number of extensions 228 within the linkage may vary, so too may the size, shape, and spacing of the voids 236. When the linkages 212 are aligned within the flexible sheath 208, the voids 236 of each of the linkages 212 can substantially align so as to define four continuous voids that extend along the length of the outer cannula 200. As shown in FIG. 27, each of the voids 236 can be configured to receive a surgical instrument 424 during intranasal endoscopy or a surgical procedure. In the depicted embodiment, the surgical instrument is an inflatable dilation balloon. However, the voids 236 can collectively receive any of various types of surgical instruments, such as irrigation cannula, suction cannula, dissection instruments, laser fibers, etc. Each of the surgical instruments 424 can have a self-straightening spring 420 disposed in or around its length, so as to automatically straighten the instrument as it extends out of the end of the outer cannula 200. This self-straightening feature aids in maintaining predictable alignment of the surgical instrument 424 so as to more easily control the location and orientation of the surgical instrument 424 through manual control of the outer cannula 200 and/or the endoscope 300, which will be discussed in detail below.

In addition to the voids 236, each of the linkages 212 can define a plurality of holes 232 that extend through the body 224. In particular, each hole 232 can extend through an entirety of each extension 228 from an anterior end to a posterior end. As depicted, each extension 228 defines a respective hole 232 so that each linkage 212 defines four separate holes 232. However, it is contemplated that each extension 228 can include more or less than one hole 232. As with the voids 236, when the linkages 212 are aligned along the length of the outer cannula 200 within the flexible sheath 208, the holes 232 can define respective continuous internal passages that extend throughout the entirety of the outer cannula 200. The holes 232 of each of the linkages 212 can thus be configured to receive respective guidewires 218. As each linkage 212 can include four holes 232, the outer cannula 200 can be configured to include four guidewires 218. However, as the number of holes 232 in each linkage can vary, the number of guidewires 218 can differ accordingly.

Figure 12A:
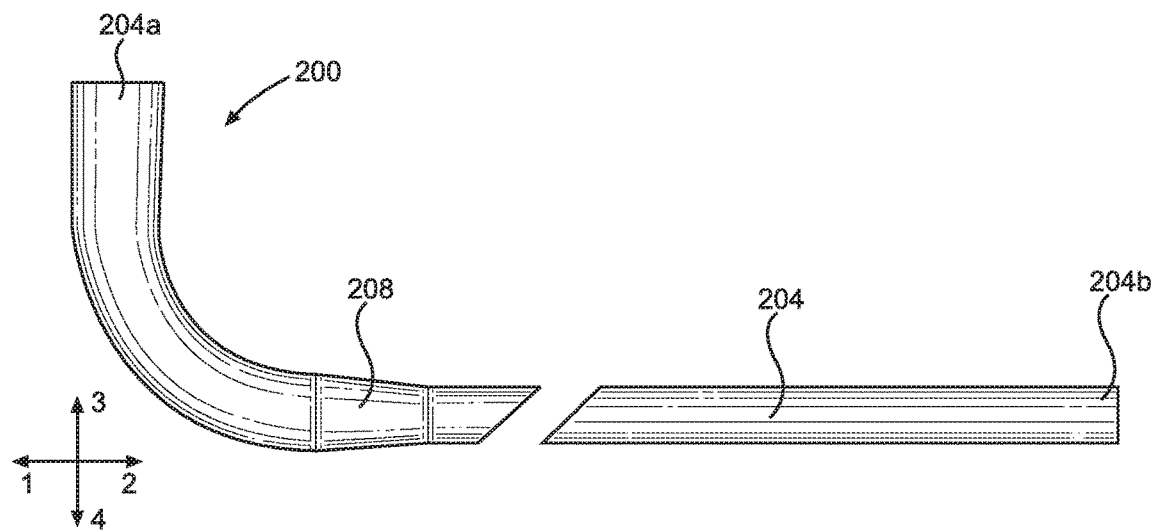
FIG. 12A is a side view of an outer cannula according to an embodiment of the present disclosure.
Figure 12B:
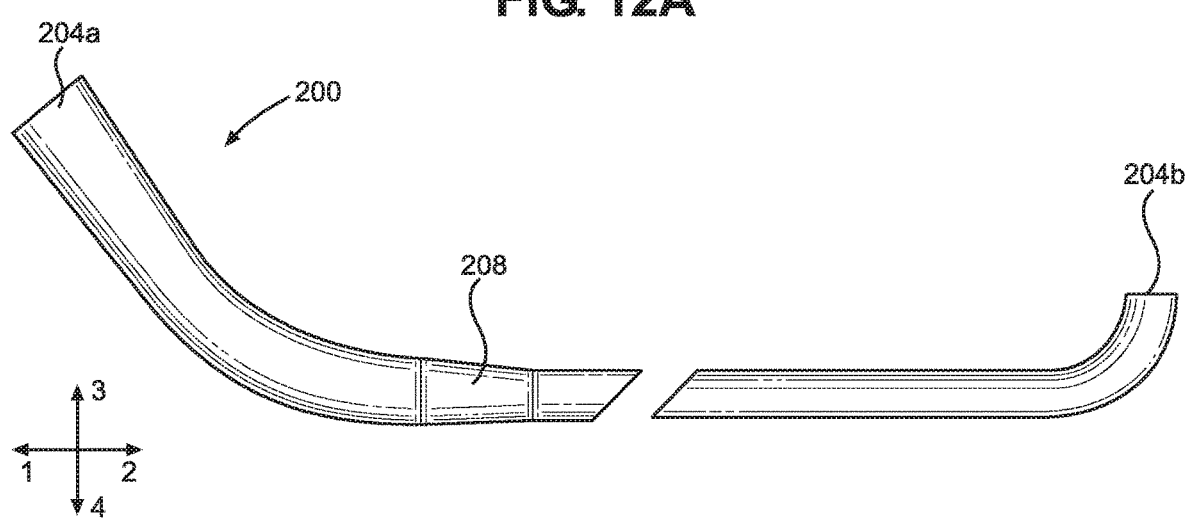
FIG. 12B is a side view of the outer cannula shown in FIG. 12A, with the body in a different configuration.
Figure 12C:
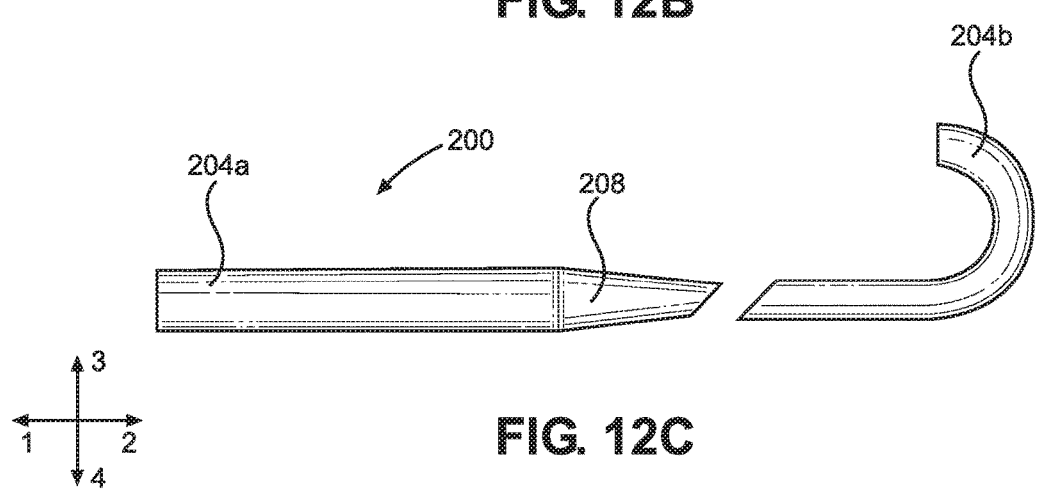
FIG. 12C is a side view of the outer cannula shown in FIG. 12A, with the body in a different configuration.
Figure 13:
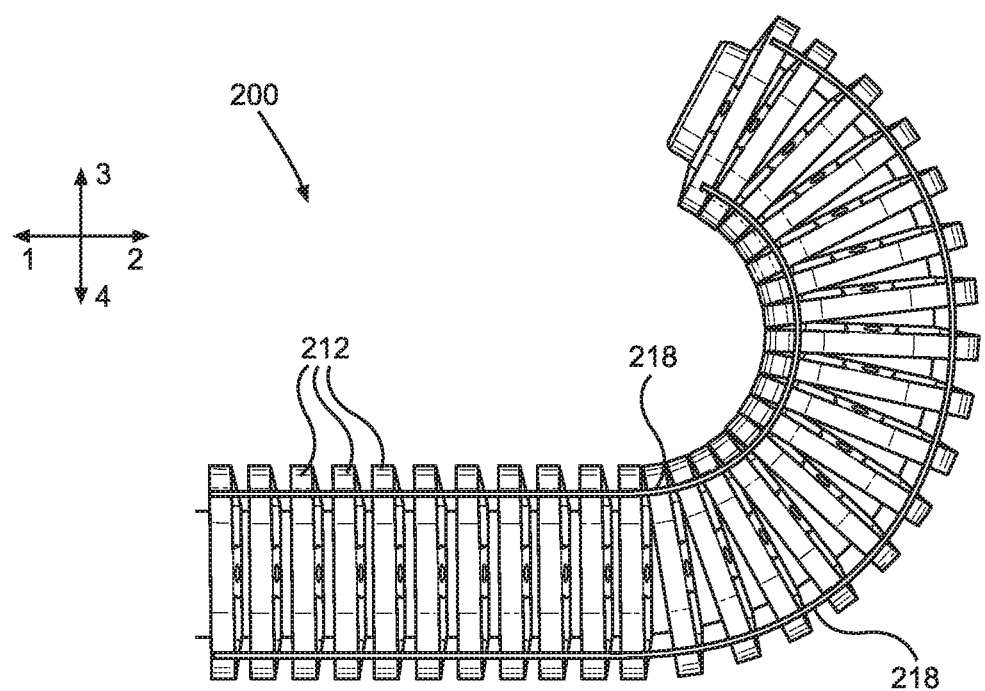
FIG. 13 is a side view of the outer cannula shown in FIG. 12A, with the outer sheath removed.
Figure 14:
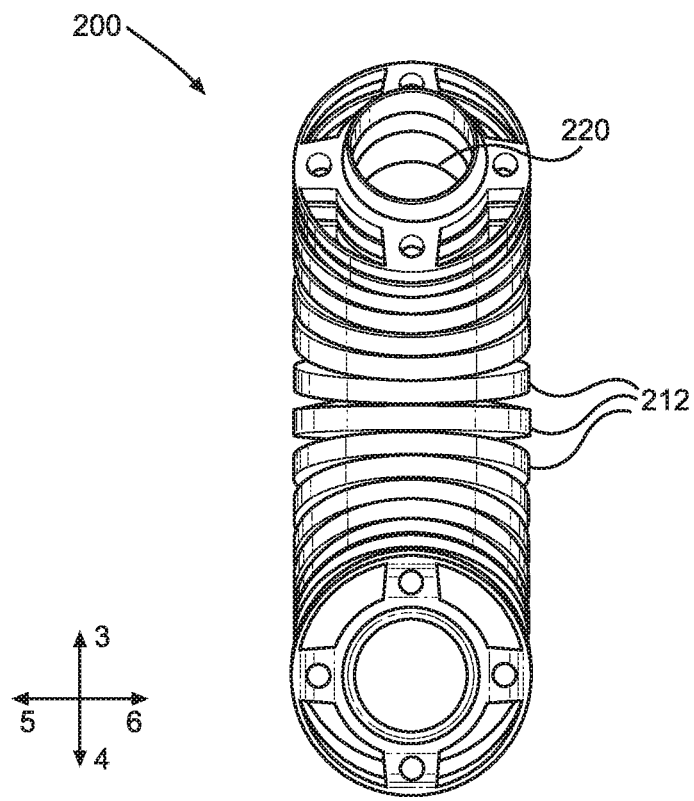
FIG. 14 is a front view of the outer cannula shown in FIG. 13.
Figure 15:
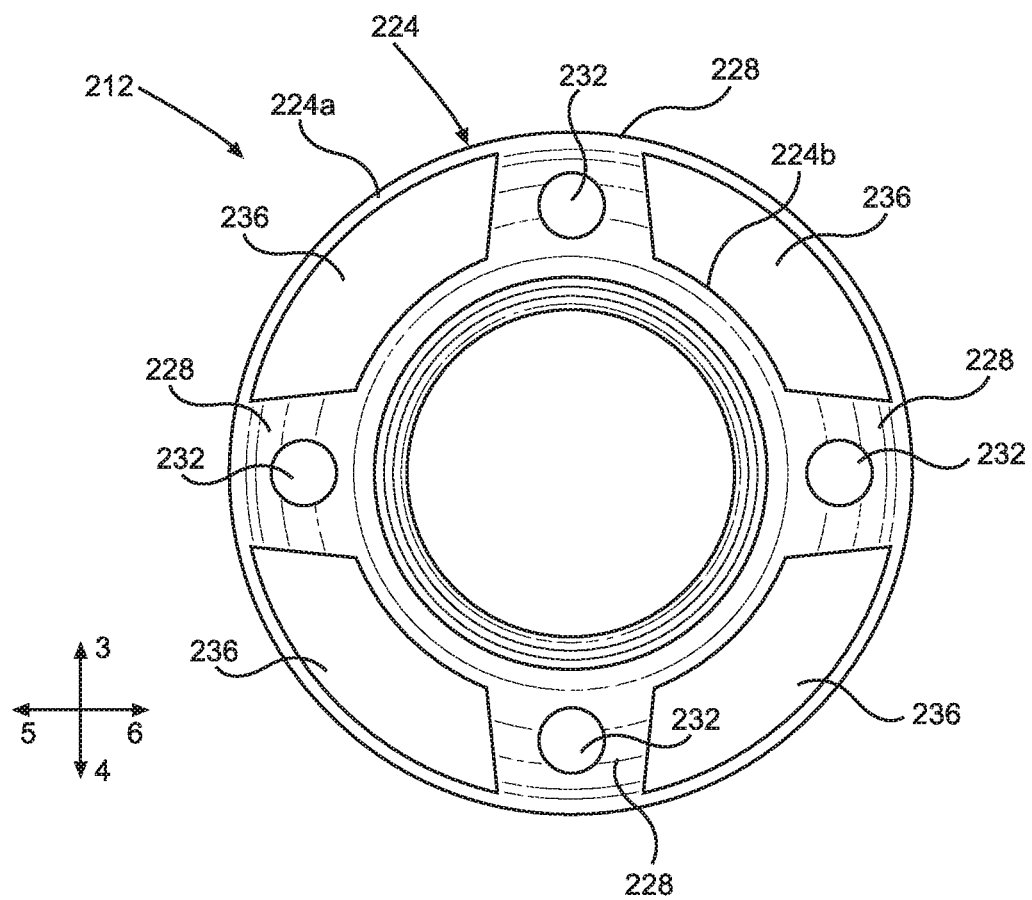
FIG. 15 is a top view of a linkage of the outer cannula shown in FIG. 12.
Figure 16:
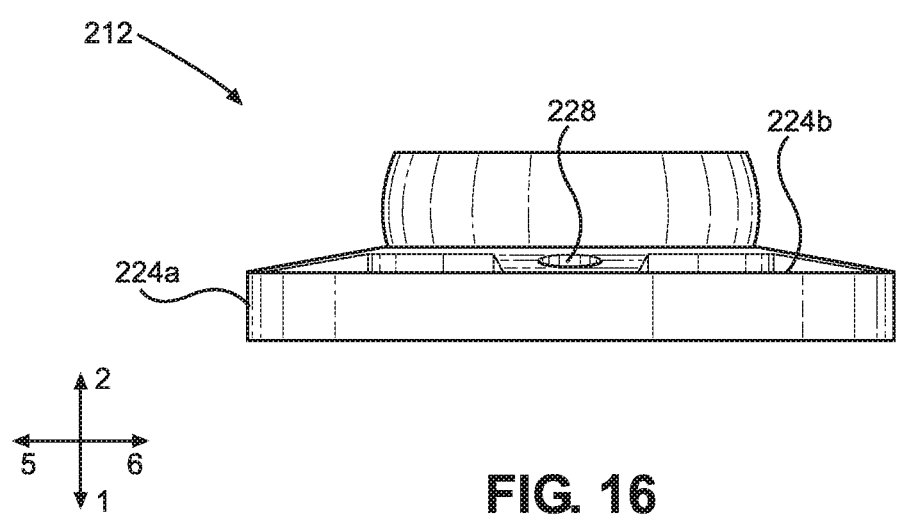
FIG. 16 is a side view of the linkage shown in FIG. 15.
Figure 17:
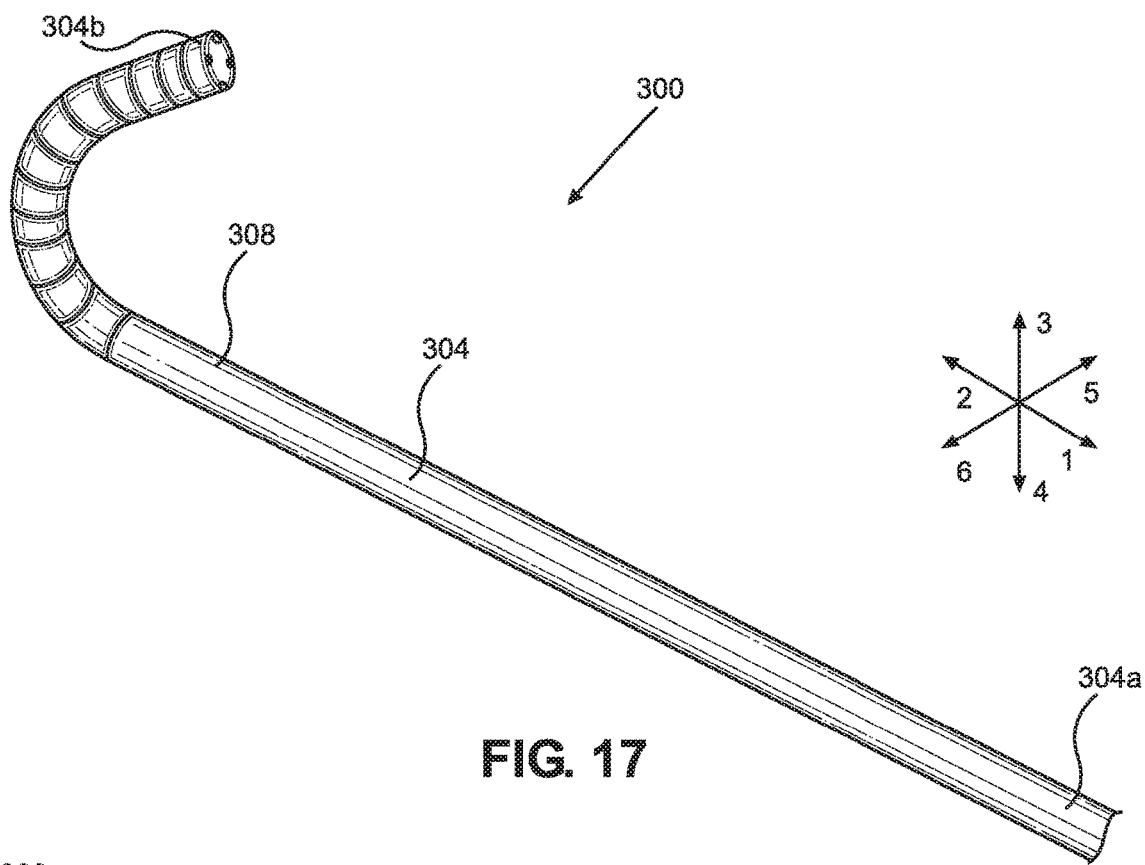
FIG. 17 is a perspective view of an endoscope according to an embodiment of the present disclosure.
Figure 18:
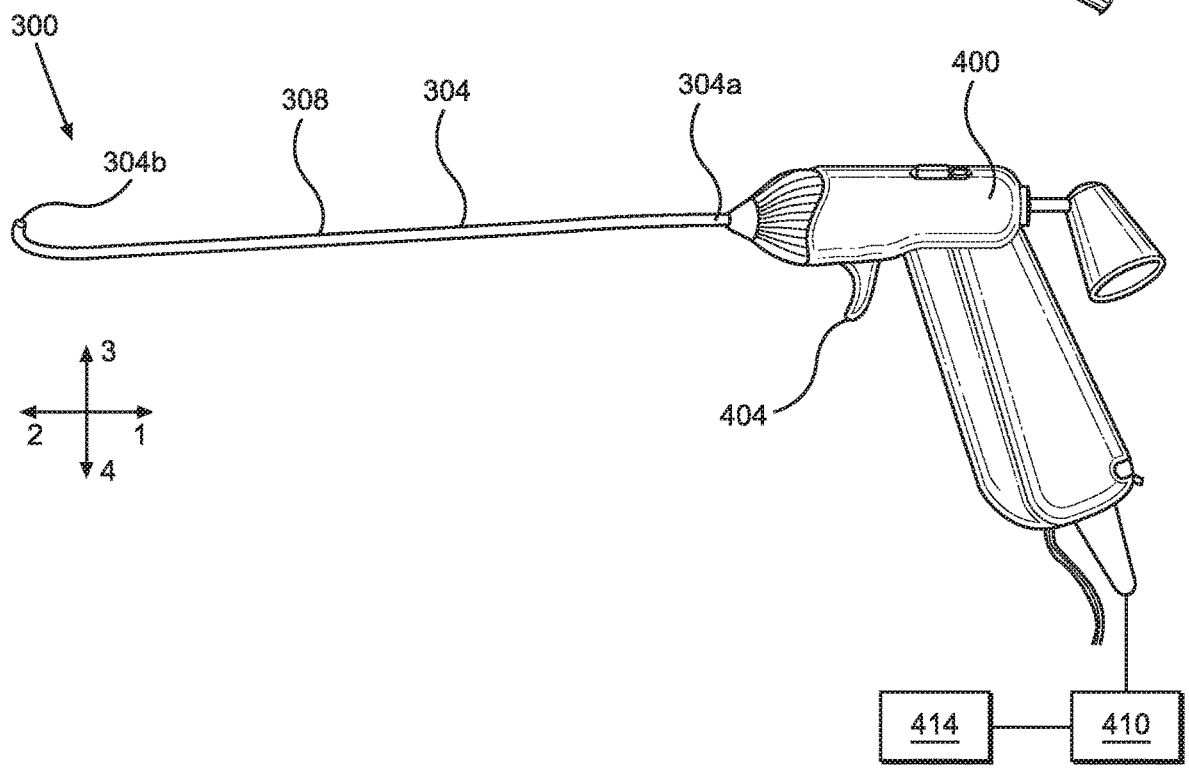
FIG. 18 is a perspective view of the endoscope shown in FIG. 17, with an actuator attached.

Each guidewire 218 can extend from the anterior end 204a of the outer cannula 200 and be fixedly attached to the linkage 212 located at the posterior end 204b of the outer cannula 200. In operation, the guidewires 218 can be utilized to control movement of the outer cannula 200 along the vertical and horizontal planes, specifically for maneuvering the outer cannula 200 around the soft palate 18 of a patient 10, as will be described further below. Movement of the guidewires 218, and thus curvature of the outer cannula 200, can be controlled manually by the hand of a user of the assembly 50, or alternatively by an actuator 400 or similar mechanical actuation means. In use, tension on any of the guidewires 218 will be applied by a user at the anterior end 204a of the outer cannula 200. Tension applied on any particular guidewire 218 at the anterior end 204a of the outer cannula 200 will cause movement of the posterior end 204b of the outer cannula 200 in the direction of that particular guidewire 218. As a result, the direction/orientation of the posterior end 204b of the outer cannula 204a can be entirely controlled by a portion of the anterior end 204a completely external to a patient. For example, tension applied to the superior-most guidewire 218 (the guidewire 218 at the "12 o'clock" position) will cause the posterior end 204b of the outer cannula 200 to move upwards in the superior direction 3, tension applied to the inferior-most guidewire 218 (the guidewire 218 at the "6 o'clock" position) will cause the posterior end 204b of the outer cannula 200 to move downwards in the inferior direction 4, tension applied to the left-most guidewire 218 (the guidewire 218 at the "9 o'clock" position) will cause the posterior end 204b of the outer cannula 200 to move left along the left direction 6, and tension applied to the right-most guidewire 218 (the guidewire 218 at the "3 o'clock" position) will cause the posterior end 204b of the outer cannula 200 to move right in the right direction 5. In addition to the above-described movements, combinations of guidewires 218 can be tensioned at once to move the posterior end 204b of the outer cannula 200 in multiple directions. In this way, the posterior end 204b of the outer cannula 200 can be curved up to at least 180 degrees, such that the outer cannula 200 substantially doubles back on itself. In one embodiment, the radius of curvature of the posterior end 204b of the outer cannula 200 can be about 18 mm. However, other radiuses of curvature are contemplated. An exemplary movement of the outer cannula 200 is shown in FIGS. 12A-12C. In FIG. 12A, the anterior end 204a of the outer cannula 200 is curved upwards along the superior direction 3 while the posterior end 204b is straight. In FIG. 12B, the anterior end 204a is slightly straightened, thus lowering the anterior end 204a along the inferior direction 4 while raising the posterior end 204b along the superior direction 3. In FIG. 12C, the anterior end 204a is fully straightened, thus causing the posterior end 204b to even further curve along the superior direction 3 until the posterior end 204b substantially defines a 180 degree curve. These equal and opposite motions can be similarly replicated along any of the superior, inferior, right, and left directions 3-6. Also, similar to the surgical instrument 424, the outer cannula 200 can include a self-straightening spring so as to automatically straighten an unrestricted portion of the body 204 of the outer cannula 200.

Now referring to FIGS. 17-27, the endoscope 300 will be discussed in detail. The endoscope 300 can have an elongate body 304 that extends from an anterior end 304a to a posterior end 304b opposite the anterior end 304a. In one embodiment, the endoscope 300 can have a pliable elastic casing defining an outer portion of the elongate body 304. During an endoscopic procedure, the anterior end 304a is configured to be located external to the patient 10 while the posterior end 304b can be located within the nasal cavity 22, and specifically inserted into the oral pharynx and then the nasopharynx, behind the soft palate and anteriorly into the posterior choana, past the septum, and into the nose and sinuses. Like the body 204 of the outer cannula 200, the body 304 of the endoscope 300 is substantially flexible, such that a user can manually adjust the curvature and orientation of various portions along the body 304, as will be discussed further below. However, the body 304 of the endoscope 300 will be sufficiently small so as to easily be disposed and translate through the central lumen 220 of the outer cannula 200. The posterior end 304b of the endoscope 300 has less resistance to movement than the portion of the endoscope 300 disposed within the mouth gag 100 and outer cannula 200.

The endoscope 300 can comprise a flexible sheath 308 that extends from the anterior end 304a to the posterior end 304b and is configured to be disposed around the internal components of the endoscope 300. The flexible sheath 308 can be comprised of a sufficiently flexible material so as to conform to the various shapes and configurations of the internal features of the endoscope 300, while sufficiently protecting and shielding those features from environmental features. The endoscope 300 can also comprise a plurality of linkages 312 disposed within the flexible sheath 308 and arranged along the flexible sheath 308. Each of the linkages 312 can be a monolithic, molded plastic or metal component. Each linkage can comprise a body 324 having a central portion 328 and extensions 330 extending radially from the central portion 328. The central portion 328 can have a substantially annular shape, though other shapes are contemplated. Also, the body 324 is shown as having four extensions 330, each being equidistantly spaced about the perimeter of the central portion 328 at the "12 o'clock," "3 o'clock," "6 o'clock," and "9 o'clock" positions. However, the body 324 can include more or less extensions as desired. For example, the body 324 can include one, two, three, or more than four extensions. Also, in other embodiments the extensions 330 may not be equidistantly spaced about the perimeter of the central portion 328.

Each linkage 312 defines a bore extending through the center of the central portion 328. When aligned within the flexible sheath 308, these bores can collectively define a central passage 322 that extends through the entirety of the endoscope 300. The central passage 322 can be configured to receive components of the emitter 344 and sensor 348, which will be discussed further below. The central portion 328 of each linkage can be tapered inwards as it extends along the posterior direction 2. This allows the posterior end of the central portion 328 of each linkage 312 to nest within the anterior end of the central portion 328 of the next linkage 312 along the length of the endoscope 300. This nesting arrangement aids in aligning the linkages 312 along the endoscope 300 and limiting the relative translation between the linkages 312, while still allowing relative rotation between adjacent linkages 312 so as to permit curving of the endoscope 300.

Each of the linkages 312 can define a plurality of holes 332 that extend through the body 324. In particular, each hole 332 can extend through an entirety of each extension 330 from an anterior end to a posterior end. As depicted, each extension 330 defines a respective hole 332 so that each linkage 312 defines four separate holes 332. However, it is contemplated that each extension 330 can include more or less than one hole 332. When the linkages 312 are aligned along the length of the endoscope 300 within the flexible sheath 308, the holes 332 can define respective continuous internal passages that extend throughout the entirety of the endoscope 300. The holes 332 of each of the linkages 312 can thus be configured to receive a respective guidewire 318. As each linkage 312 can include four holes 332, the endoscope 300 can be configured to include four guidewires 318. However, as the number of holes 332 in each linkage 312 can vary, the number of guidewires 318 can differ accordingly.

Figure 22:
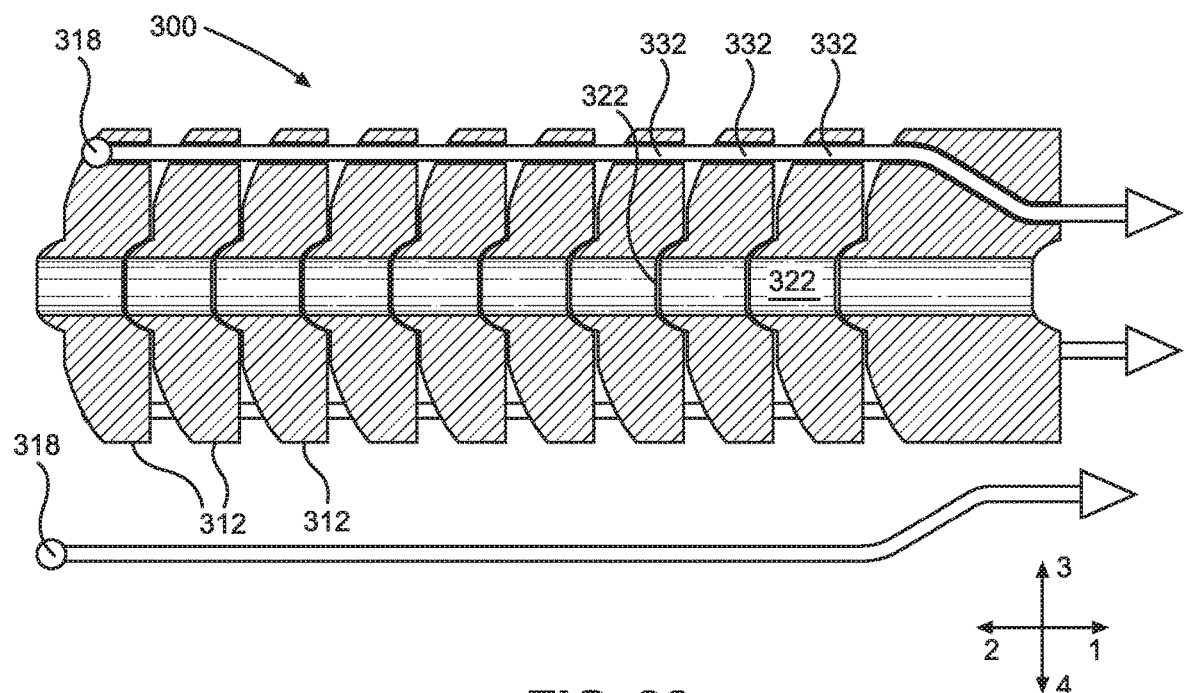
FIG. 22 is a cross-sectional view of the endoscope shown in FIG. 19.

As shown in FIG. 22, each guidewire 318 can extend from the anterior end 304a of the endoscope 300 and be fixedly attached to the linkage 312 located at the posterior end 304b of the endoscope 300. In operation, the guidewires 318 can be utilized to control movement of the endoscope 300 along the vertical and horizontal planes, specifically for maneuvering the endoscope 300 within the nasal cavity 22 of a patient 10, as will be described further below. Movement of the guidewires 318, and thus curvature of the endoscope 300, can be controlled manually by the hand of a user of the assembly 50, or alternatively by an actuator 400 (FIG. 18) or similar mechanical actuation means. In the depicted embodiment, the actuator 400 is a gun-type actuator, and actuation is performed through actuation of an interface 404, which may be a trigger. However, other types of actuators are contemplated, such as keyboards, joysticks, etc. In use, tension on any of the guidewires 318 will be applied by a user at the anterior end 304a of the endoscope 300. Tension applied on any particular guidewire 318 at the anterior end 304a of the endoscope 300 will cause movement of the posterior end 304b of the endoscope 300 in the direction of that particular guidewire 318. For example, tension applied to the superior-most guidewire 318 (the guidewire 318 at the "12 o'clock" position) will cause the posterior end 304b of the endoscope 300 to move upwards in the superior direction 3, tension applied to the inferior-most guidewire 318 (the guidewire 318 at the "6 o'clock" position) will cause the posterior end 304b of the endoscope 300 to move downwards in the inferior direction 4, tension applied to the left-most guidewire 318 (the guidewire 318 at the "9 o'clock" position) will cause the posterior end 304b of the endoscope 300 to move left along the left direction 6, and tension applied to the right-most guidewire 318 (the guidewire 318 at the "3 o'clock" position) will cause the posterior end 304b of the endoscope 300 to move right in the right direction 5. In addition to the above-described movements, combinations of guidewires 318 can be tensioned at once to move the posterior end 204b of the endoscope 300 in multiple directions. In this way, the posterior end 304b of the endoscope 300 can be curved up to at least 180 degrees, such that the endoscope 300 substantially doubles back on itself. Also, similar to the surgical instrument 424, the endoscope 300 can include a self-straightening spring 319 so as to automatically straighten an unrestricted portion of the body 304 of the endoscope 300. Because the outer cannula 200 and the endoscope 300 each contain their own set of respective, independent guidewires 218, 318, each of the outer cannula 200 and the endoscope 300 can be curved and otherwise manipulated by a user of the assembly 50 independently and separately. Though guidewires 218, 318 are explicitly described as utilized for controlling the outer cannula 200 and endoscope 300, respectively, in other embodiments other devices can be used for controlling the outer cannula 200 and endoscope 300, such as micromanipulators, for example.

Figure 23:
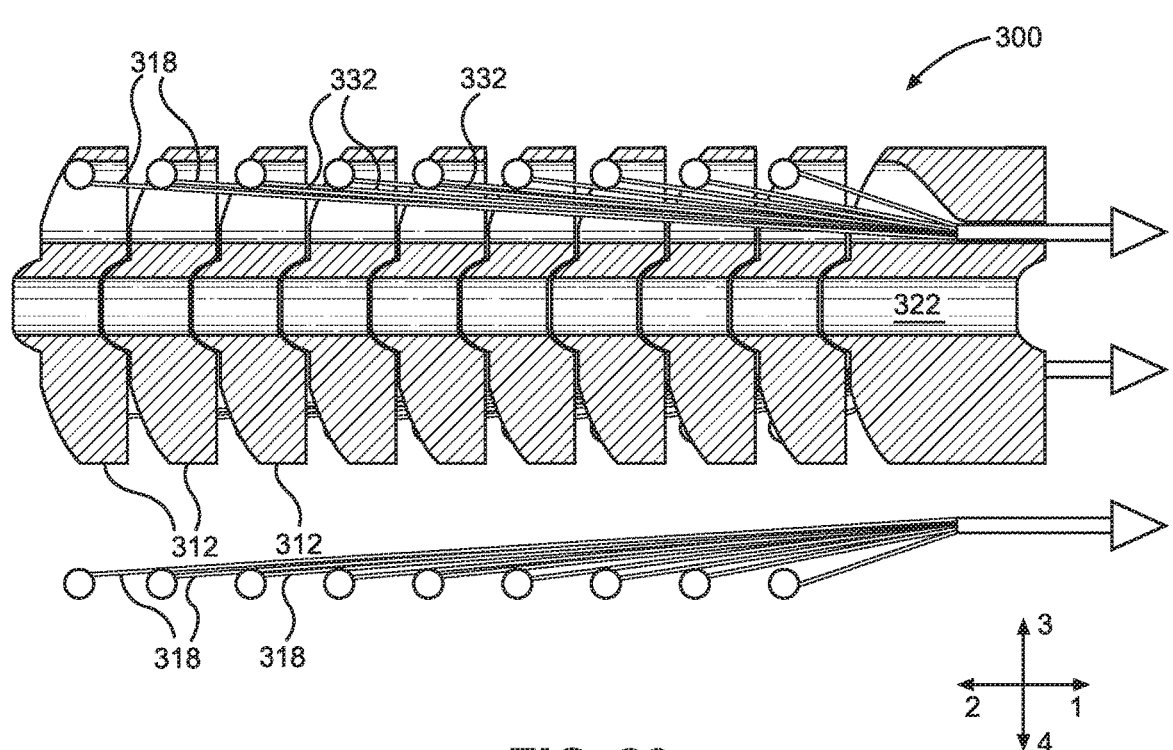
FIG. 23 is an alternative cross-sectional view of the endoscope shown in FIG. 19.
Figure 24A:
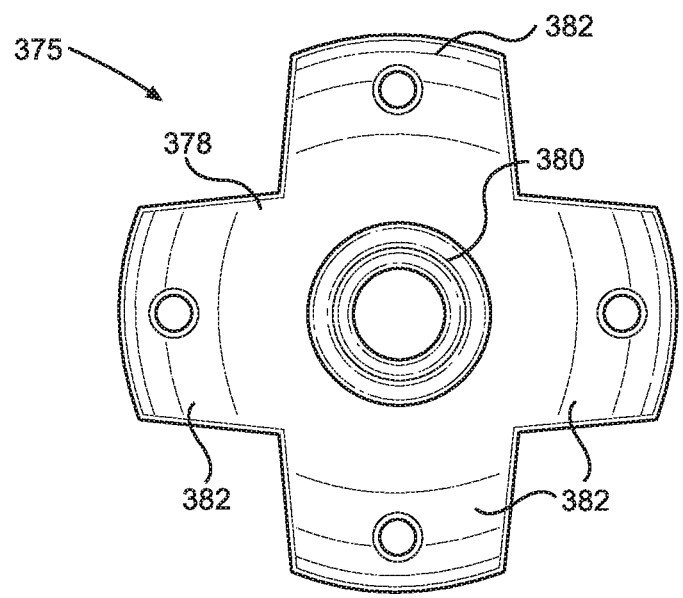
FIG. 24A is a top view of a linkage according to another embodiment of the present disclosure.
Figure 24B:
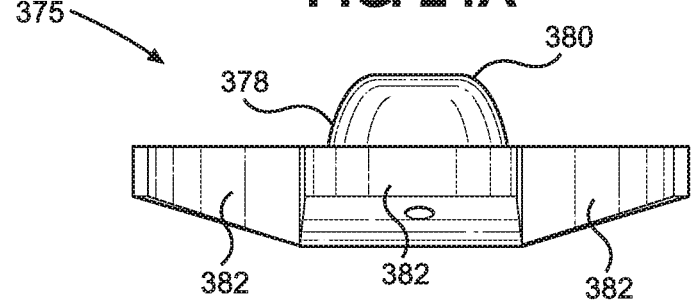
FIG. 24B is a side view of the linkage shown in FIG. 24A.
Figure 24C:
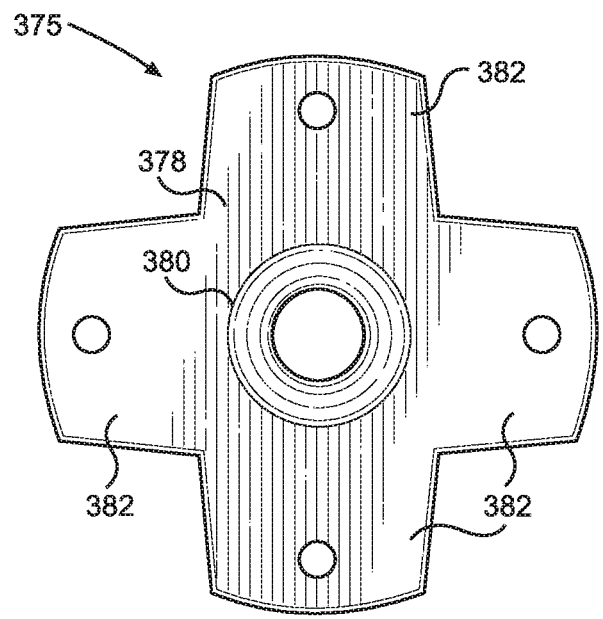
FIG. 24C is a bottom view of the linkage shown in FIG. 24A.

With reference to FIG. 23, in another embodiment the endoscope 300 can include more than four guidewires 318. In this embodiment, each linkage 312 is depicted as having four respective guidewires 318 attached thereto. This increased number of guidewires 318 that are attached to multiple locations along the length of the endoscope 300 can provide a user of the assembly 50 with an improved ability to cause curvature of the endoscope 300 at locations between the anterior end 304a and the posterior end 304b. This can be done by tensioning guidewires 318 that attach to a particular linkage 312 located between the anterior end 304a and the posterior end 304b. Though FIG. 23 shows each linkage 312 as having four respective guidewires 318 attached thereto, in further embodiments the endoscope 300 can include guidewires 318 attached to any number or configuration of the linkages 312.

Figure 26:
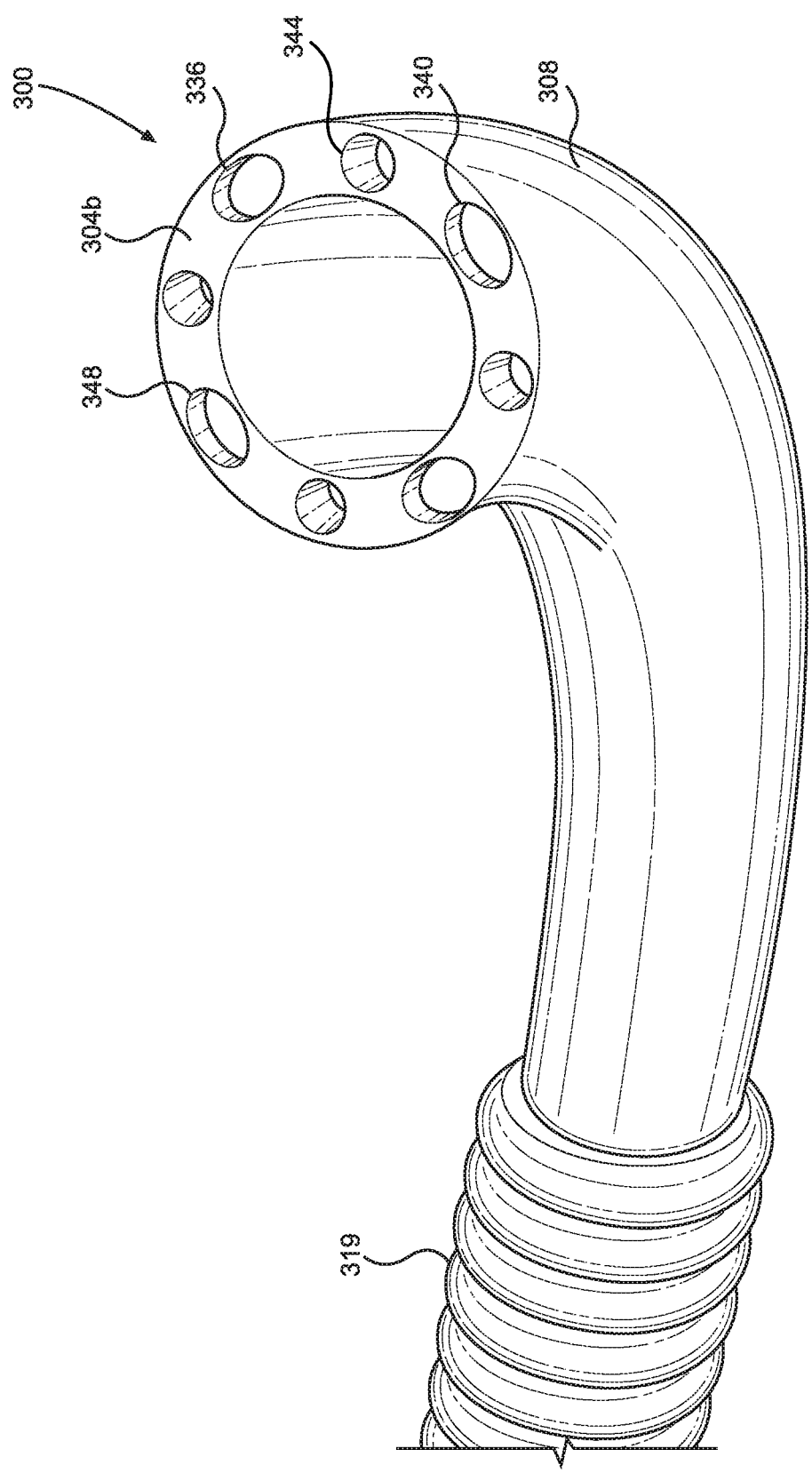
FIG. 26 is a perspective view of a posterior end of an endoscope according to an embodiment of the present disclosure.

Referring to FIG. 26, the posterior end 304b of the endoscope 300 is shown in detail. The emitter 344 and sensor 348 can be centrally disposed about the posterior end 304b of the endoscope 300. As such, curving of the endoscope 300 through tensioning of the guidewires 318 is performed with the ultimate goal of directing the posterior end 304b such that the emitter 344 and sensor 348 can optimally view a desired anatomical structure of the patient 10. In one embodiment, the emitter 344 can be a light, such as an LED, and the sensor 348 can be a camera. However, the emitter 344 and sensor 348 can employ other methods for analyzing and imaging the anatomical structure, such as through ultrasound or EM waves. The sensor 348 can be positioned so that the sensor 348 has a range of view embodying a 90 degree cone. The emitter 344 and sensor 348 are connected through the central passage 322 of the endoscope 300 to the actuator 400, and ultimately to a visual output 414. The visual output 414 is thus configured to receive and process an output signal from the sensor 348. The visual output 414 can be a monitor or any such device capable of providing visual output, and allows the operator of the assembly 50 to view the interior of the nasal cavity 22 as viewed by the sensor 348 in preparation for and during a surgical procedure, as well as to help guide movement of the endoscope 300 within the patient 10. Because the endoscope 300 may bend 180 degrees within a patient 10, the field of vision of the sensor 348 may be inverted relative to the vantage point of the operator. As such, the output of the sensor 348 can be processed by an inversion circuit 410 electrically connected between the sensor 348 and the visual output 414 so as to invert the output of the sensor 348 as necessary to maintain a constant output orientation displayed by the visual output 414. The posterior end 304b can also contain a conduit baffle 340 configured to direct fluid across the emitter 344 and sensor 348, as well as a conduit 336 configured to remove the fluid from the working area. This allows a user to selectively clean the sensor 348 and emitter 344 and/or clear debris from the visual field. Though one sensor 348 and one emitter 344 are shown, it is contemplated that the posterior end 304b of the endoscope 300 can include an array comprising a plurality of sensors and emitters.

Figure 25A:
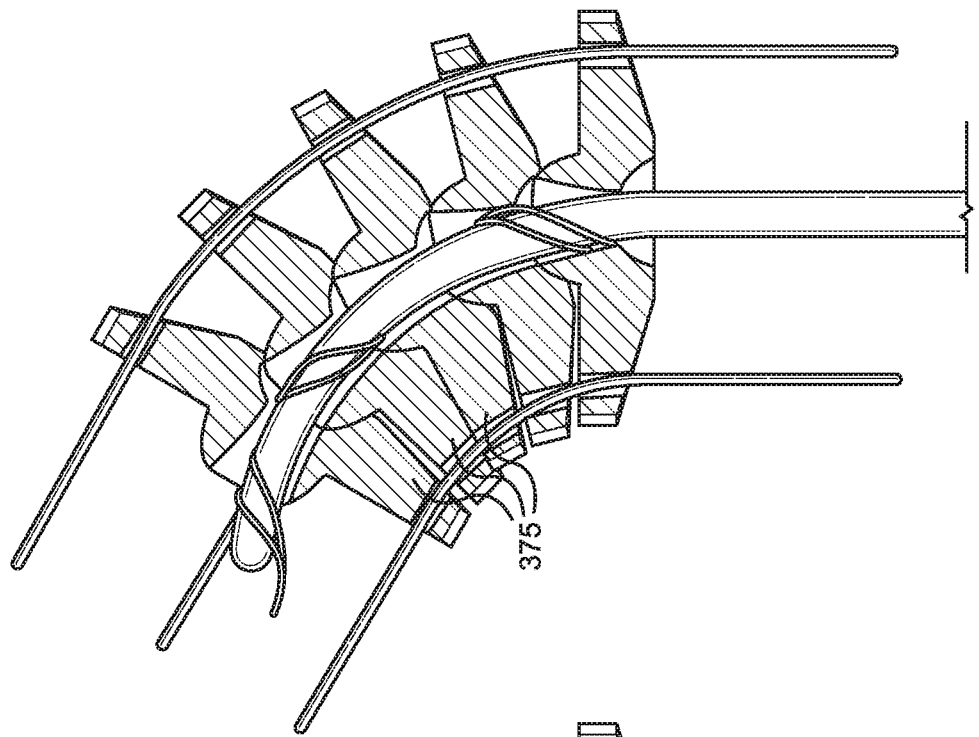
FIG. 25A is a partial side view of an endoscope according to the present disclosure comprising linkages as shown in FIG. 24A.
Figure 25B:
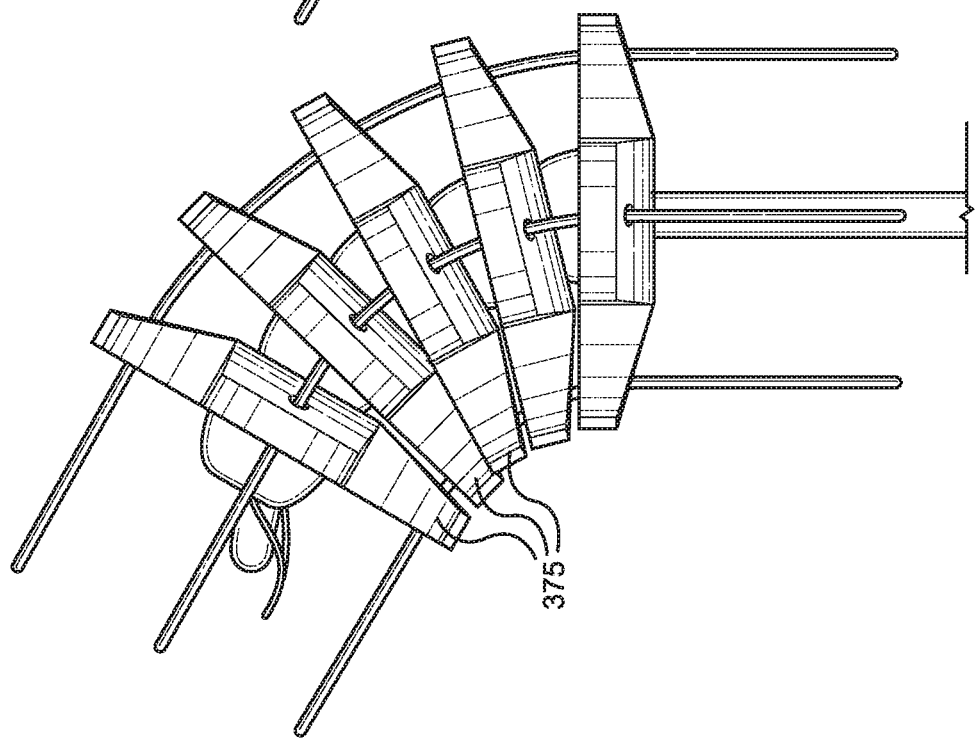
FIG. 25B is a partial side cross-sectional view of the endoscope shown in FIG. 25A.

FIGS. 24A-25B show an additional embodiment of a linkage 375 usable in the endoscope 300 according to an embodiment of the present disclosure. Each of the linkages 375 can be a monolithic, molded plastic or metal component. Each linkage can comprise a body 378 having a central portion 380 and extensions 382 extending radially from the central portion 328. The central portion 328 can have a substantially annular shape, though other shapes are contemplated. Each linkage 375 can allow for 15 degrees of rotation in both the 'x' and 'y' planes, and the semi-spherical construction allows for potential axial twisting. Though 15 degrees of rotation is specifically described, each linkage 375 can allow alternative degrees of rotation as desired. The guide wires of the endoscope 300 and the flexible casing can provide stabilizing structure to prevent twisting. FIGS. 25A-25B show the linkages 375 at maximum curvature. The central lumen is shown as transmitting a fiberoptic fiber and electrical camera connections. The apertures for each linkage form a smooth walled tunnel that minimizes damage to the wires.

Figure 28:
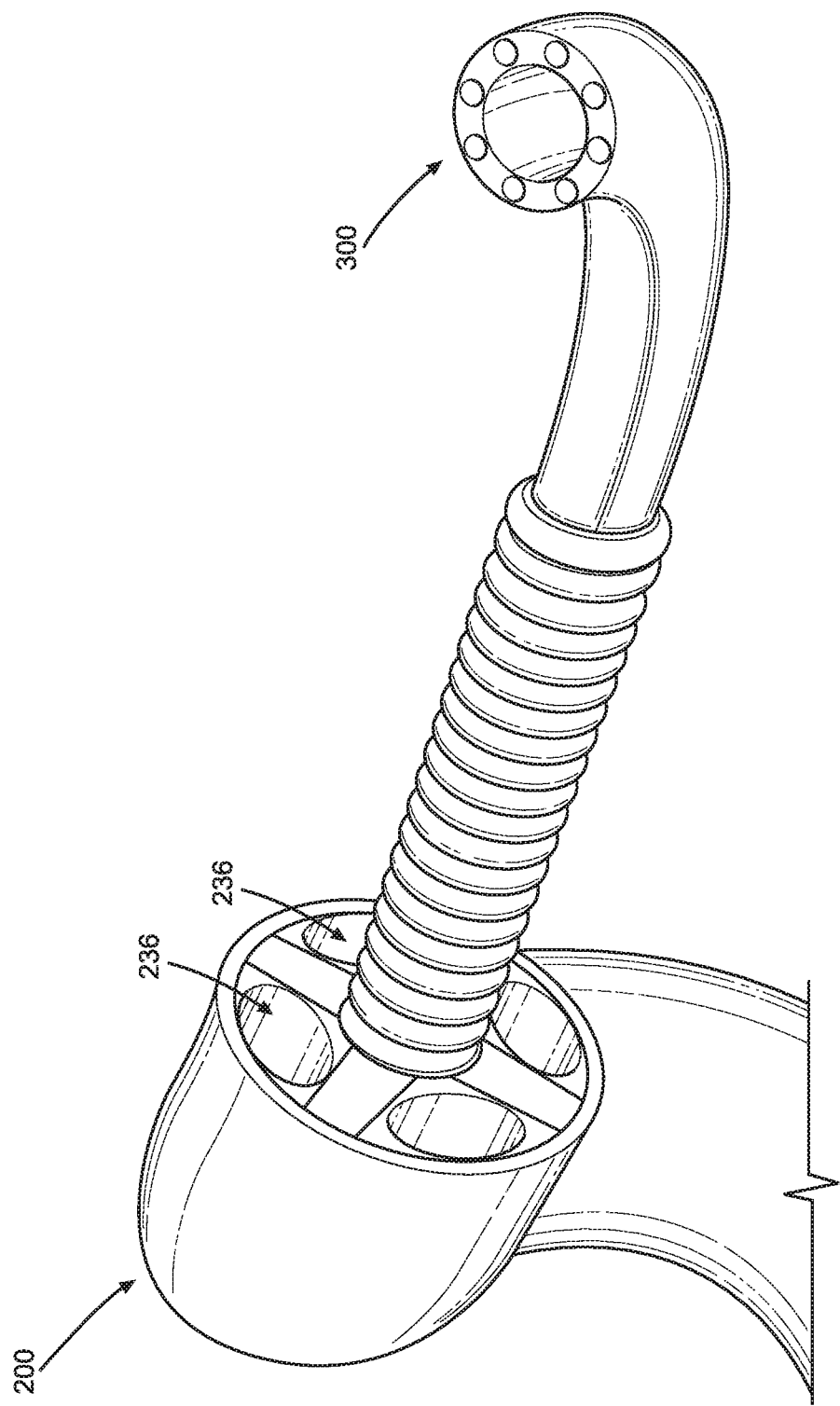
FIG. 28 is a perspective view of an endoscope and outer cannula according to an embodiment of the present disclosure.
Figure 29:
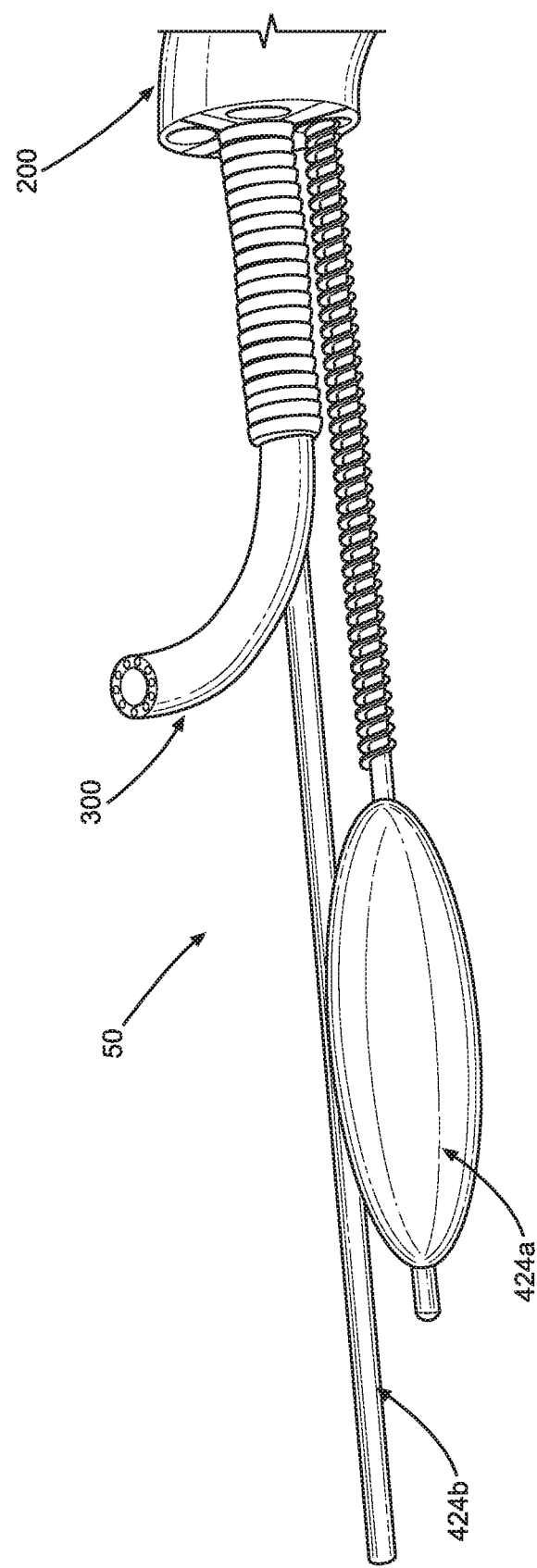
FIG. 29 is an alternative side view of the assembly shown in FIG. 27.

FIG. 28 shows a close up view of the endoscope 300 emerging from the outer cannula 200. Visible are the plurality of voids 236 in the outer cannula 200 that allow for the introductory of accessory instrumentation. FIG. 30 shows the endoscope 300 and outer cannula 200 with first and second accessory instruments 424a, 424b. In the depicted embodiment, the first accessory instrument 424a can be a dilating balloon on a self-straightening stalk, while the second accessory instrument 424b can be a laser fiber, which because of its inherent stiffness does not require additional elements for rigidity. However, other accessory instruments are contemplated in place of or in addition to the first and second accessory instruments 424a, 424b.

Figure 30A:
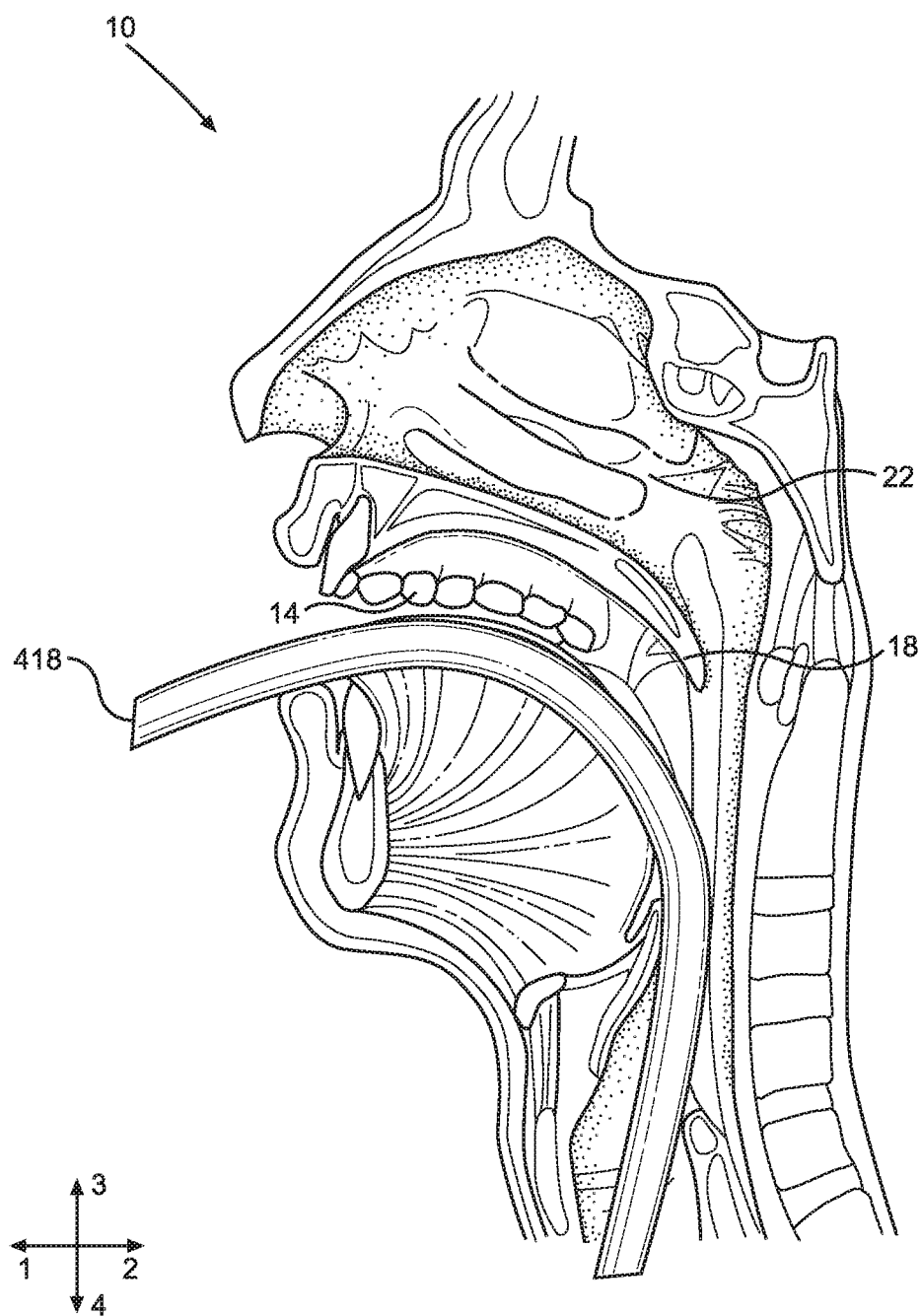
FIG. 30A is a side cross-sectional view of a nasal cavity of a patient, with an endotracheal tube inserted.
Figure 30B:
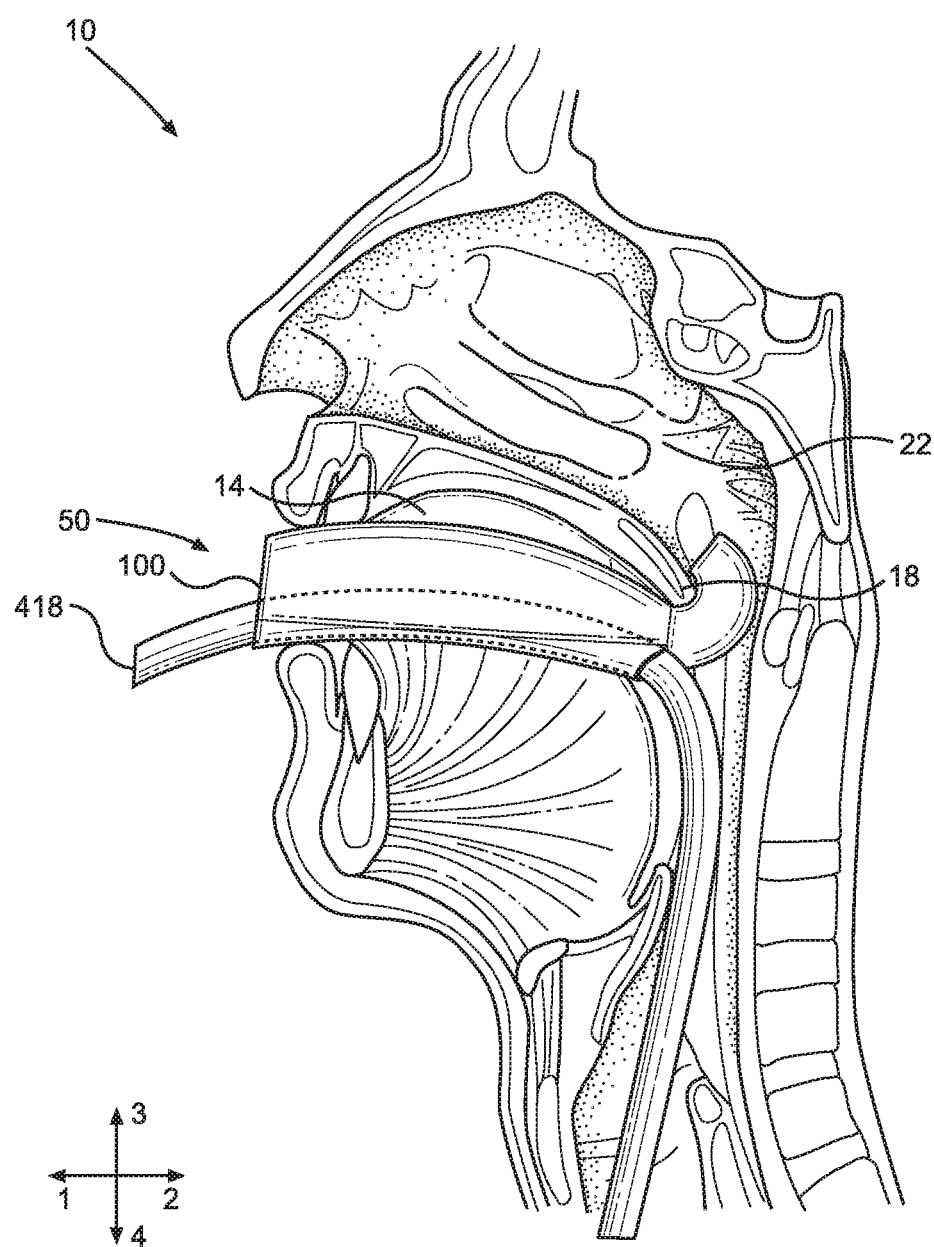
FIG. 30B is a side cross-sectional view of the nasal cavity shown in FIG. 30A, with a mouth gag in place.
Figure 30C:
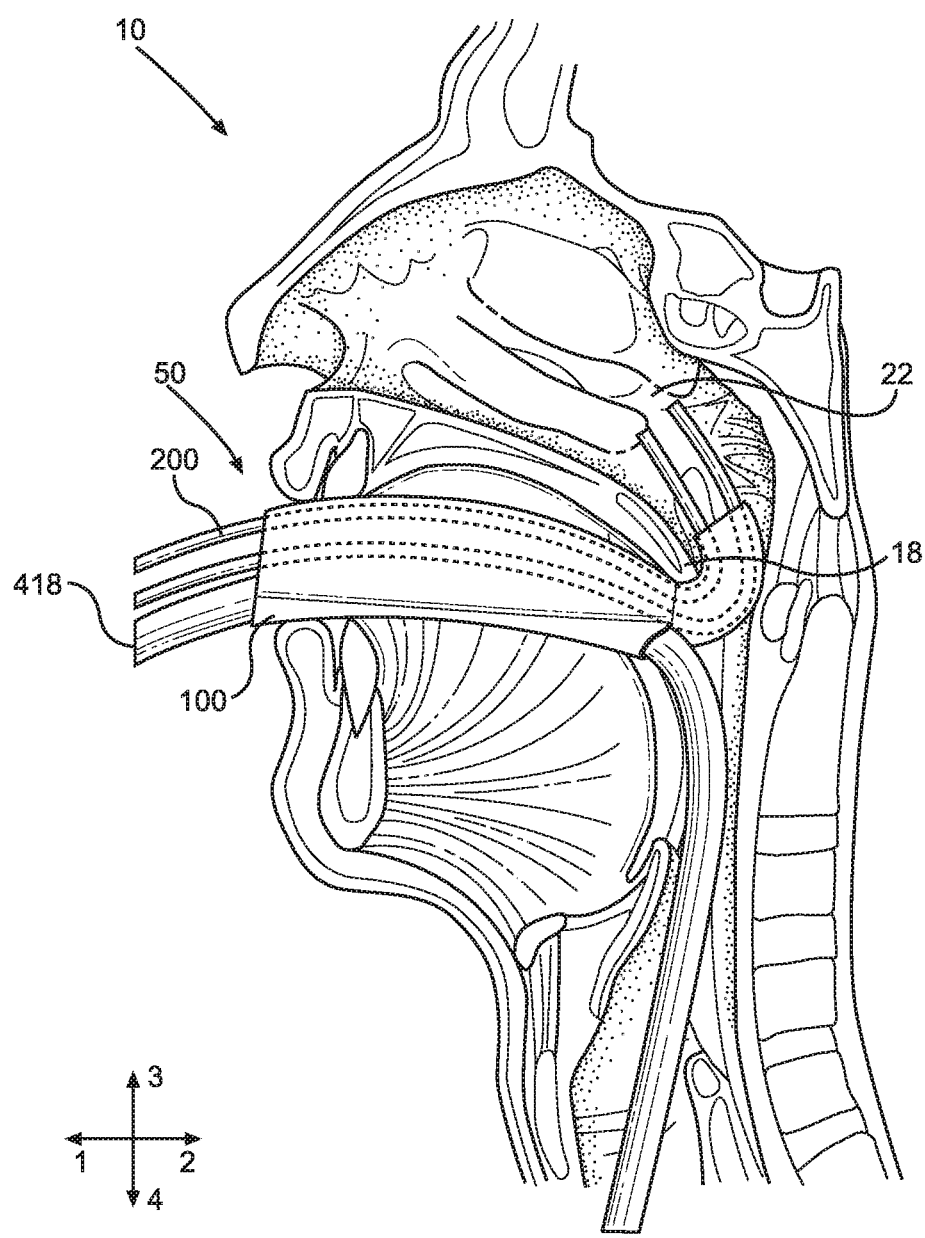
FIG. 30C is a side cross-sectional view of the nasal cavity shown in FIG. 30A, with an outer cannula in place.
Figure 31:
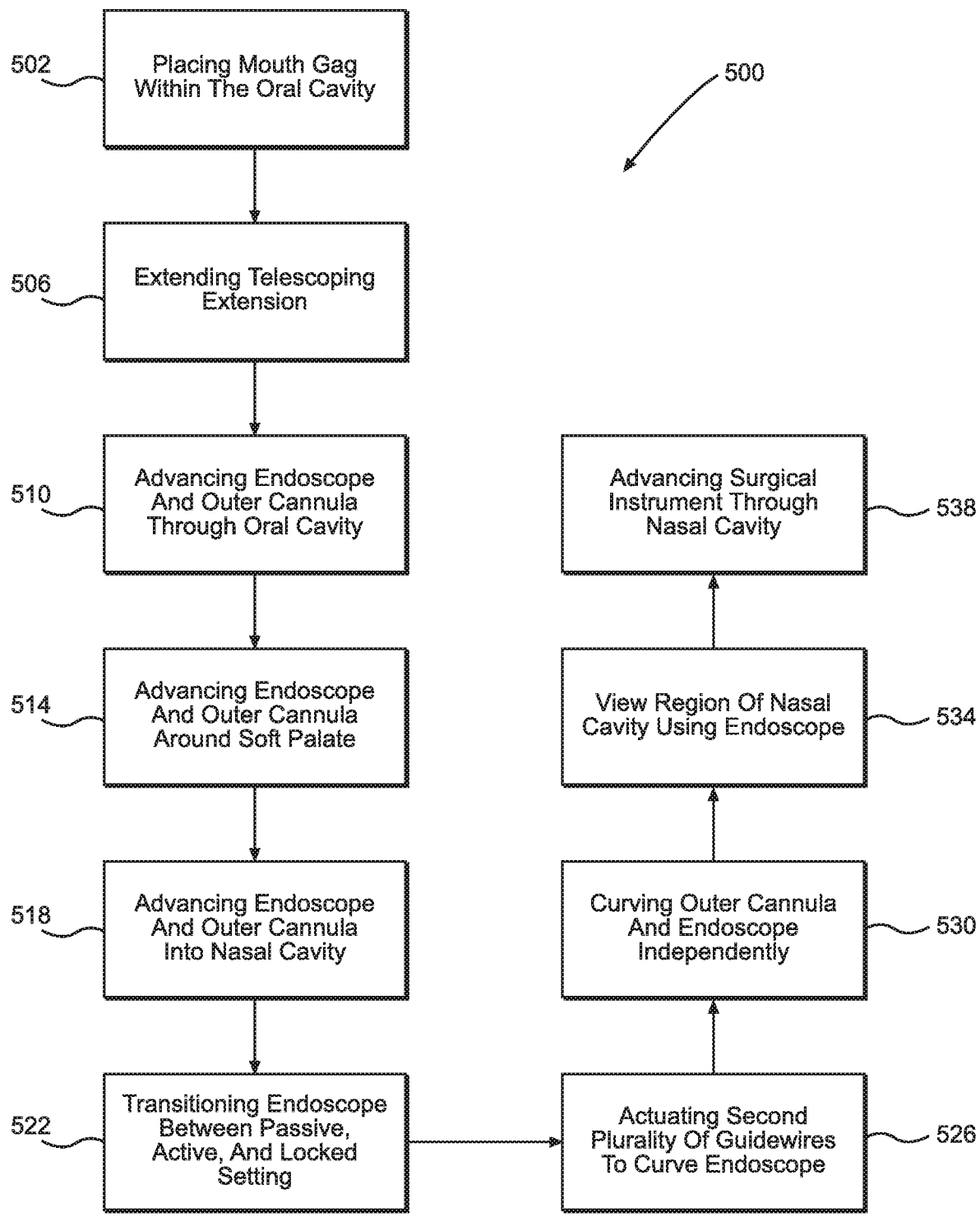
FIG. 31 is a process flow diagram of a method of performing intranasal endoscopy according to an embodiment of the present disclosure.

Referring to FIG. 31, a method 500 of performing intranasal endoscopy using the assembly 50 will be described. Initially, an endotracheal tube 418 can be inserted posteriorly through the oral cavity 14 of the patient 10 so as to ensure a clear air passage exists throughout the intranasal endoscopy procedure (as shown in FIG. 30A). Currently, endoscopic sinus surgeries are performed using the nasal aperture as the entry point to the sinuses rather than a posterior approach. After the endotracheal tube 418 has been properly placed, step 502 can be performed, in which the main body 104 of the mouth gag 100 can be placed within the oral cavity 14 of the patient 10 such that the outer groove 120 of the mouth gag 100 is positioned over and secures the endotracheal tube 418 in place (as shown in FIG. 30B). After the main body 104 is in place, in step 506 a user can extend the telescoping extension 108 that is attached to the posterior end 104b of the main body 104 into a nasopharynx of the patient 10. Specifically, this involves extending the telescoping extension 108 around the soft palate 18. Extension of the telescoping extension 108 can be performed using crank 180, or any other similar tool.

After the mouth gag 100 is in place and the telescoping extension 108 has been extended, the outer cannula 200 and the endoscope 300 can be inserted into the patient 10. Before this is done, the endoscope 300 can be inserted into the central lumen 220 of the outer cannula 200 so that the endoscope 300 and outer cannula 200 can be inserted as a unit. However, it is configured that in other embodiments outer cannula 200 can be fully inserted first, followed by the endoscope 300.

In step 510, the outer cannula 200 and the endoscope 300 are advanced in the posterior direction 2 through the oral cavity 14. As the main body 104 of the mouth gag 100 is positioned within the oral cavity 14, this step also involves advancing the outer cannula 200 and the endoscope 300 through the central cavity 116 of the mouth gag 100. After the outer cannula 200 and the endoscope 300 have passed through the oral cavity 14, the outer cannula 200 and the endoscope 300 can be advanced upwards around a soft palate 18 of the patient in step 514. As the telescoping extension 108 of the mouth gag 100 extends around the soft palate 18, this step also involves advancing the outer cannula 200 and the endoscope 300 through the telescoping extension 108. Because the telescoping extension 108 is curved, the outer cannula 200 and the endoscope 300 must similarly be curved by a user as the outer cannula 200 and endoscope 300 pass from the main body 104, through the telescoping extension 108, and out the output opening 116b of the central cavity 116. As noted above, curvature at the posterior end 204b of the outer cannula 200 in a desired direction can be achieved by curving the anterior end 204a in the opposite direction. As a result, step 514 can also involve actuating a plurality of the guidewires 218 of the outer cannula 200 so as to curve the outer cannula 200.

During the method 500, the endoscope 300, and specifically the guidewires 318 of the endoscope 300, can be transitioned between a plurality of settings using the interface 404 or other device connected to the actuator 400. Specifically, the guidewires 318 can be transitioned between a passive setting, an active setting, and a locked setting. Each of these settings is designed to be used in particular stage of the endoscope insertion process, as will be discussed further below. In the passive setting, the guidewires 318 are not being controlled by a user and allow the endoscope 300 to move freely. This setting is useful during steps 510, 514, and 518 when the endoscope 300 is disposed within the outer cannula 200 and the endoscope 300 and outer cannula 200 are being inserted together through the mouth gag 100, around the soft palate 18, and into the nasal cavity 22. As the outer cannula 200 is the primary component being manipulated during this process, the endoscope 300 must be free to conform to the shape of the outer cannula 200 as the outer cannula 200 is moved and curved by the user. The active and locked settings will be useful in subsequently disclosed steps, and will accordingly be described below.

Figure 30D:
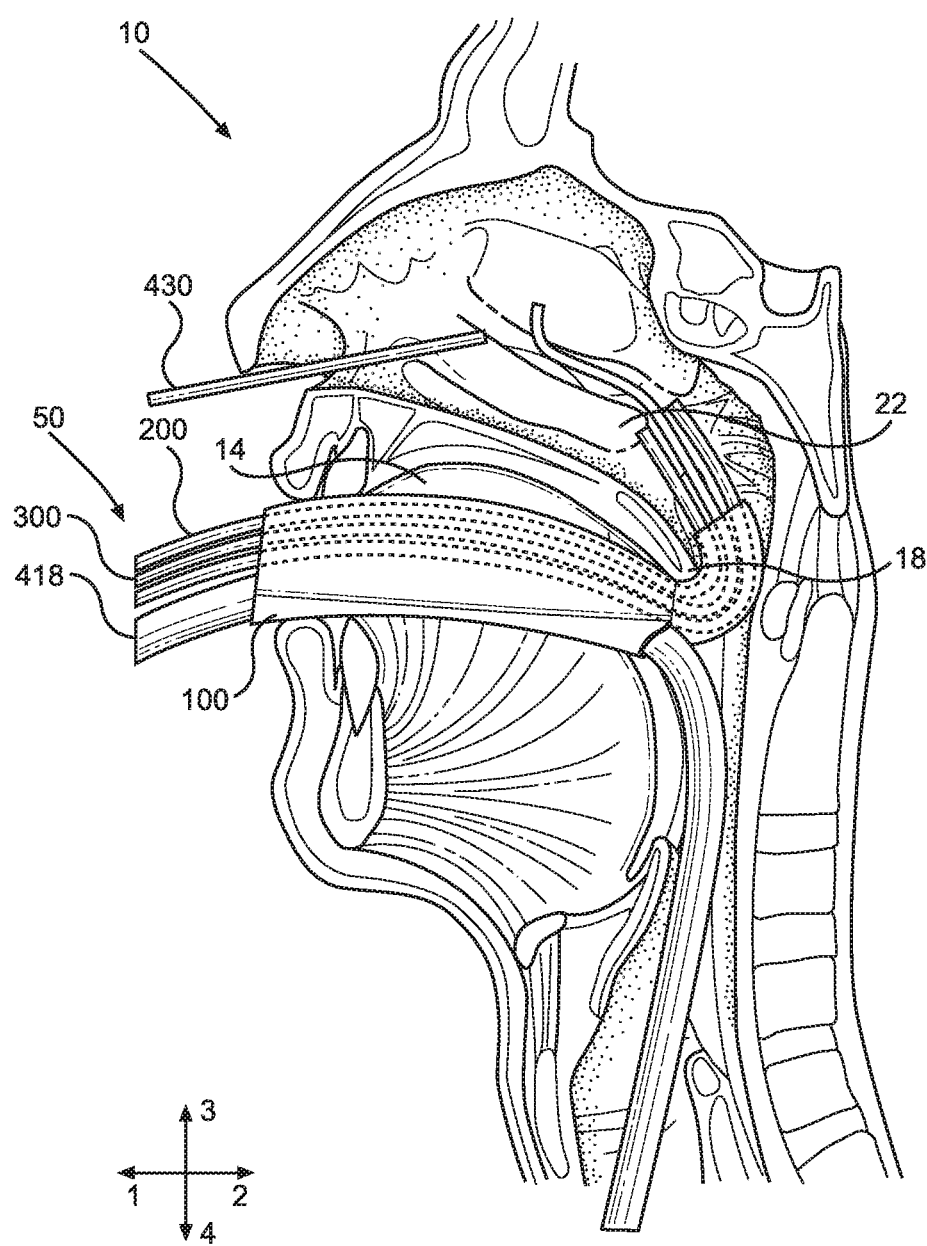
FIG. 30D is a side cross-sectional view of the nasal cavity shown in FIG. 30A, with an endoscope in place.

After step 514, in step 518 the outer cannula 200 and the endoscope 300 can be advanced in the anterior direction 1 into the nasal cavity 22 of the patient 10 (shown in FIG. 30D). At this point, the outer cannula 200 has reached its maximum level of insertion, and the endoscope 300 can be advanced beyond the posterior end 204b of the outer cannula 200 and transitioned from the passive setting to the active setting and locked setting in step 522. In the active setting, the curve of a portion of the endoscope that extends beyond the outer cannula 200 is capable of being adjusted through the interface 404 of the actuator 400. This curve is performed in step 526, in which the plurality of guidewires 318 of the endoscope 300 are actuated so as to curve the endoscope 300. The user of the assembly 50 performs this step so as to locate and view an anatomical structure of interest within the nasal cavity 22. To aid in this operation, the user may also desire to curve the plurality of guidewires 218 of the outer cannula 200. As such, the user can perform step 530, in which the outer cannula 200 and the endoscope 300 are curved separately by the user using their respective guidewires 218, 318.

Once the desired anatomical structure has been located, the endoscope can be transitioned into a locked setting, in which the guidewires 318 are locked in place, and likewise the curve of the portion of the endoscope 300 that extends beyond the outer cannula 200 is locked into place. Then, the emitter 344 and sensor 348 can be utilized to obtain an image of the anatomical structure and send an output to the visual output 414. Then, in step 534 a user can view a region of the nasal cavity 22 using the endoscope 300 and the visual output 414. The information gained from viewing the anatomical region of the nasal cavity 22 can be useful in planning a surgical procedure, guiding a surgical instrument 430 into a correct position, and performing a subsequent surgical operation. As such, in step 538, a surgical instrument 430 can be inserted into the nasal cavity 22 along the posterior direction 2, and a surgical operation can then be performed.

Figure 32:
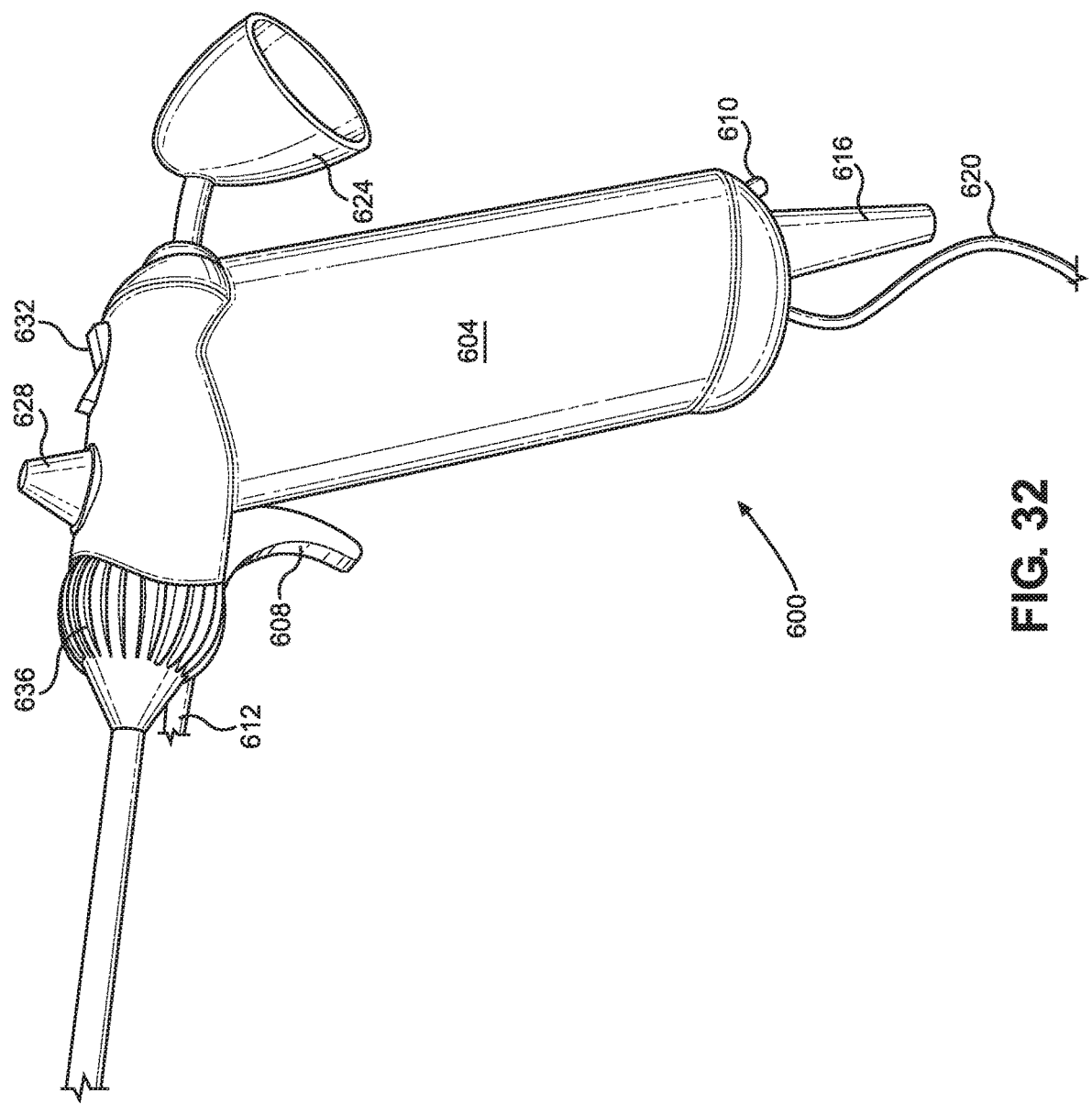
FIG. 32 is a side view of a handpiece according to an embodiment of the present disclosure.

FIG. 32 depicts a handpiece 600 capable of controlling the endoscope 300. The handpiece 600 is capable of detecting the amount of endoscope flexion to assist with image orientation. The handpiece 600 includes controls for comfortably physically orienting the handpiece 600 to the inner endoscope, electronically rotationally orienting the image, irrigating the sensor, irrigating the operative field (with a variable temperature irrigation fluid), suction (internal or external tubing), and a manually switchable image inversion control. The handpiece 600 can also have wireless image transmission abilities. Specifically, the handpiece 600 can include a body 604 and a trigger 608 for actuating irrigation controls from an irrigation inlet port 610 through an irrigation outlet port 612. The base of the handpiece 600 can include a suction port 616 and at least one electrical cord 620 extending therefrom. The handpiece 600 can further include a joystick connection 624 for operator control. The handpiece 600 can include additional controls, such as a knob 628 for image rotation control, a switch 632 for image inversion or vertical motion, and/or an endoscope rotation knob 636 with a conical adapter for an irrigation sheath. The electronics and motors contained within the handpiece 600 can be removable and packaged/contained in a magazine. This magazine is then able to be removed and appropriately sterilized separately from the remaining components of the handpiece 600. When the magazine is inserted in to the handpiece 600, there are electrical couplings and gears which mesh with the components within the handpiece 600 allowing for complete operation of the handpiece 600.

Within the handle of the handpiece 600 can be paired spools of tensioning wire. These wires extend the length of the endoscope 300 at 12, 3, 6, and 9 o'clock positions. They can be paired with the 6 and 12 locations, and the 3 and 9 o'clock locations. These spools can have three working conditions. The first condition is when the handle is activated to direct the scope, the spools are controlled so that one spool of the pair rotates to release wire while the paired spool collects an approximately equal amount of wire. The difference in arcs of curvatures must be accounted for in the amount of collected and released wire. This causes the distal end of the endoscope 300 to bend towards the tensioning side. The second condition is when the handle of the handpiece 600 is activated but not directing the tip of the endoscope 300, there is constant relatively high equal tension on both of the pairs. This equal tension locks the controllable portion of the scope in its present configuration. In the third condition, the handpiece 600 is placed in is a non-activated or passive condition. This condition is used when the fully flexible endoscope 300 is being passively directed through the outer cannula such as when the scope ensemble is placed through the nasopharyngeal extension of the mouth gag 100 or when the inner endoscope 300 is individually being placed into the outer cannula 200. In this condition the paired spools are placed under a relatively lower tension but are all free to rotate independently. This lower tension is designed to allow the endoscope 300 to bend and conform to its new configuration but permit the guide wires within to move but yet avoid any laxity of the wires. This tension does not cause the endoscope 300 to lock. When the handle is then activated, the present new set of rotated conditions of the spools can define the new starting point for controlling the endoscope 300. When the conditions of two paired wire spools indicate that the inner endoscope 300 is flexed more than a certain amount, image inversion can be detected and an automatic correction can take place. If the automatic correction is not desired, there can be a manual inversion switch 632 which can be used to select non-inversion. The handpiece additionally can have a knob 628 to electronically orient any rotational corrections necessary to maintain the correct anatomic orientation of the image on the monitor. The image can be transmitted wirelessly or hardwired. The electronic circuit would also have the capacity to merge individually produced images, if multiple sensor arrays are used, into a single image. The tip of the fully flexible endoscope 300 may also have a small appendage which could be used to help externally guide any accessory instruments which had been advanced through the outer cannula. The extra maneuverability and flexibility of the endoscope 300 tip, along with its imaging ability, would make placement of these accessory instruments more precise.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts, and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features, and concepts may be expressly identified herein as being inventive or forming part of an invention, such identification is not intended to be exclusive, but rather there may be inventive aspects, concepts, and features that are fully described herein without being expressly identified as such or as part of a specific invention, the scope of the inventions instead being set forth in the appended claims or the claims of related or continuing applications. Descriptions of exemplary methods or processes are not limited to inclusion of all steps as being required in all cases, nor is the order that the steps are presented to be construed as required or necessary unless expressly so stated.

While the invention is described herein using a limited number of embodiments, these specific embodiments are not intended to limit the scope of the invention as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in a particular order as desired.

What is claimed:

1. An assembly for performing intranasal endoscopy on a patient, the assembly comprising:
    a mouth gag comprising a main body defining a central cavity and a telescoping extension attached to the main body, the telescoping extension configured to transition between a collapsed state and an expanded state, wherein the main body is configured to be at least partly received in an oral cavity of the patient and the telescoping extension is configured to be received in a nasopharynx of the patient while the main body is within the oral cavity of the patient;
    an outer cannula defining a central lumen, wherein the outer cannula is configured to be introduced through the central cavity of the main body; and
    an endoscope extending through the central lumen of the outer cannula and configured to be advanced into a nasal cavity or a sinus of the patient.

2. The assembly of claim 1, wherein the outer cannula and the endoscope are configured to be curved independently from each other.

3. The assembly of claim 1, wherein:
    the main body extends from a posterior end to an anterior end, and
    the telescoping extension is attached to the posterior end.

4. The assembly of claim 1, wherein the telescoping extension has a unitary, expandable body.

5. The assembly of claim 1, wherein the telescoping extension comprises:
    a first extension body; and
    a second extension body interlocked with the first extension body and moveable relative to the first extension body.

6. The assembly of claim 1, wherein the main body defines an outer wall that has an inner side facing the central cavity and an outer side opposite the inner side, wherein the outer side defines a groove configured to receive an endotracheal tube or a flexible laryngeal mask airway tube.

7. The assembly of claim 1, wherein the mouth gag includes a mechanism for transitioning the telescoping extension from the collapsed state to the expanded state.

8. The assembly of claim 1, wherein the telescoping extension extends from the main body to a leading end, wherein the leading end includes an inflatable balloon cuff.

9. The assembly of claim 1, wherein the outer cannula comprises:
    a flexible sheath; and
    a plurality of linkages disposed within the flexible sheath and arranged along the flexible sheath.

10. The assembly of claim 9, wherein the outer cannula extends from an anterior end disposed outside the patient to a posterior end positioned within the patient, wherein the outer cannula further comprises a plurality of guidewires that extend from the anterior end through a corresponding plurality of holes defined by each of the plurality of linkages to the posterior end, and the plurality of guidewires are fixedly attached to the one of the plurality of linkages at the posterior end.

11. The assembly of claim 10, wherein the anterior end of the outer cannula is moveable such that a portion of the outer cannula defines at least a 180 degree curve.

12. The assembly of claim 10, wherein the plurality of holes are four holes, and the plurality of guidewires are four guidewires.

13. The assembly of claim 10, wherein each of the plurality of linkages defines a plurality of voids for receiving a surgical instrument, such that the surgical instrument can extend through the outer cannula.

14. The assembly of claim 13, wherein the surgical instrument comprises an inflatable dilation balloon, an irrigation cannula, a suction cannula, at least one dissection instrument, or laser fibers.

15. The assembly of claim 13, wherein the plurality of voids are four voids.

16. The assembly of claim 1, wherein the endoscope includes a resilient portion that extends beyond the outer cannula that is configured to straighten after the resilient portion is curved.

17. The assembly of claim 1, wherein the endoscope comprises:
a flexible sheath; and
a plurality of linkages disposed within the flexible sheath and arranged along the flexible sheath.

18. The assembly of claim 1, wherein the endoscope extends from an anterior end positioned outside the patient to a posterior end positioned within the patient, and the endoscope further includes an emitter and a sensor at the posterior end.

19. The assembly of claim 18, further comprising:
a visual output connected to the sensor; and
an inversion circuit connected to the sensor and the visual output, wherein the inversion circuit is configured to automatically invert an output from the sensor so as to maintain a constant output orientation on the visual output.

20. The assembly of claim 1, further comprising:
an actuator connected to the endoscope, wherein the actuator includes an interface configured to allow for curving of the endoscope by a user.

21. The assembly of claim 20, wherein the endoscope is configured to be actuated between 1) a passive setting, wherein a shape of the endoscope freely conforms to a shape of the outer cannula, 2) an active setting, wherein a curve of a portion of the endoscope that extends beyond the outer cannula is capable of being adjusted through the interface of the actuator, and 3) a locked position, wherein the curve of the portion of the endoscope that extends beyond the outer cannula is locked.

* * * * *